(12) United States Patent
Gavryushin et al.

(10) Patent No.: US 9,427,406 B2
(45) Date of Patent: Aug. 30, 2016

(54) SUSTAINED-RELEASE FORMULATION

(71) Applicant: NanoScape AG, Planegg (DE)

(72) Inventors: Andrey Gavryushin, Planegg (DE); Johannes Kobler, Planegg (DE); Juergen Sauer, Planegg (DE)

(73) Assignee: Nautilus Capital Corporation, Wilmington, DE (US)

( * ) Notice: Subject to any disclaimer, the term of this patent is extended or adjusted under 35 U.S.C. 154(b) by 0 days.

(21) Appl. No.: 14/512,412

(22) Filed: Oct. 11, 2014

(65) Prior Publication Data

US 2015/0079184 A1 Mar. 19, 2015

Related U.S. Application Data

(63) Continuation-in-part of application No. PCT/EP2013/057714, filed on Apr. 11, 2013.

(30) Foreign Application Priority Data

Apr. 13, 2012 (GB) .................................. 1206547.0
Nov. 5, 2012 (GB) .................................. 1220556.3

(51) Int. Cl.
| | |
|---|---|
| *A61K 9/16* | (2006.01) |
| *A61K 47/02* | (2006.01) |
| *A61K 9/14* | (2006.01) |
| *C01B 33/18* | (2006.01) |
| *A61K 31/7036* | (2006.01) |

(52) U.S. Cl.
CPC ............... *A61K 9/1611* (2013.01); *A61K 9/143* (2013.01); *A61K 9/1652* (2013.01); *A61K 9/1682* (2013.01); *A61K 31/7036* (2013.01); *A61K 47/02* (2013.01); *C01B 33/18* (2013.01); *C01P 2004/03* (2013.01); *C01P 2004/61* (2013.01); *C01P 2006/17* (2013.01); *Y10S 977/773* (2013.01); *Y10S 977/906* (2013.01)

(58) Field of Classification Search
None
See application file for complete search history.

(56) References Cited

U.S. PATENT DOCUMENTS

| | | | |
|---|---|---|---|
| 3,994,439 | A | 11/1976 | Van Breen et al. |
| 6,265,389 | B1 | 7/2001 | Burke |
| 6,576,264 | B1 | 6/2003 | Henriksen et al. |
| 6,821,928 | B2 | 11/2004 | Ruskin |
| 7,563,451 | B2 | 7/2009 | Lin et al. |
| 7,767,004 | B2 | 8/2010 | Sayari et al. |
| 2003/0175347 | A1 | 9/2003 | Steffier et al. |

(Continued)

FOREIGN PATENT DOCUMENTS

| | | |
|---|---|---|
| EP | 000000218148 A1 | 4/1987 |
| GB | 00001206547 A | 9/1970 |

(Continued)

OTHER PUBLICATIONS

S Che, Y Sakamoto, O Terasaki, T Tatsumi. "Control of Crystal Morphology of SBA-1 Mesoporous Silica." Chemistry of Materials, vol. 13, 2001, pp. 2237-2239.*

(Continued)

*Primary Examiner* — Isaac Shomer
(74) *Attorney, Agent, or Firm* — Blakely, Sokoloff, Taylor & Zafman LLP

(57) ABSTRACT

A substantially monodisperse assemblage of particles 10 having interconnected pores 20 and a core 30 with at least one shell 40, 60 disposed about the core 30 as well as a method for their synthesis is disclosed.

30 Claims, 24 Drawing Sheets

(56) References Cited

U.S. PATENT DOCUMENTS

| | | |
|---|---|---|
| 2006/0018966 A1 | 1/2006 | Lin et al. |
| 2006/0154069 A1* | 7/2006 | Lin et al. ............... 428/402 |
| 2009/0165515 A1 | 7/2009 | Aoki et al. |
| 2009/0304756 A1 | 12/2009 | Daehne et al. |
| 2012/0251825 A1 | 10/2012 | Yang et al. |

FOREIGN PATENT DOCUMENTS

| | | |
|---|---|---|
| GB | 000001220556 | 1/1971 |
| JP | 2006347849 A | 12/2006 |
| JP | 002007096565 A | 12/2007 |
| WO | 0012619 A1 | 3/2000 |
| WO | 2005009602 A3 | 2/2005 |
| WO | 2006106493 A1 | 10/2006 |
| WO | 2009010945 A2 | 1/2009 |
| WO | 2009088250 A2 | 7/2009 |
| WO | WO 2011008939 A2 * | 1/2011 |

OTHER PUBLICATIONS

Y Hu, Z Zhi, Q Zhao, C Wu, P Zhao, H Jiang, T Jiang, S Wang. "3D cubic mesoporous silica microsphere as a carrier for poorly soluble drug carvedilol." Microporous and Mesoporous Materials, vol. 147, 2012, pp. 94-101, Available Online Jun. 13, 2011.*

Merriam-Webster Dictionary Online. Definition of "Restriction." http://www.merriam-webster.com/dictionary/restriction, accessed Aug. 19, 2015, 4 printed pages.*

VSY Lin, DR Radu, MK Han, W Deng, S Kuroki, BH Shanks, M Pruski. "Oxidative Polymerization of 1,4-Diethynylbenzene into Highly Conjugated Poly(phenylene butadiynylene) within the Channels of Surface-Functionalized Mesoporous Silica and Alumina Materials." Journal of the American Chemical Society Communications, vol. 124, 2002, pp. 9040-9041.*

VSY Lin, CY Lai, J Huang, SA Song, S Xu. "Molecular Recognition Inside of Multifunctionalized Mesoporous Silicas: Toward Selective Fluorescence Detection of Dopamine and Glucosamine." Journal of the American Chemical Society, vol. 123, 2001, pp. 11510-11511.*

"Polymeric Delivery systems for controlled Drug Release" by R. Langer in "Chemical Engineering Communications", 1980, Seiten 1-48.

"Nanostructure mediated drug delivery" by G.A. Hughes in "Nanomedicine",2005, Seiten 22-30.

"Ordered mesoporous materials" by U. Ciesla, F Schueth in "Ordered mesoporous materials" vol. 27, 1999, Seiten 131-149.

"Unique uptake of acid-prepared mesoporous spheres by lung epithelial and mesothelioma cells" by Blumen et al in" American Journal of Respiratory Cell and Molecular Biology" vol. 36 No. 3, 2007, Seiten 333-342.

"Dimensionless presentation for drug release from a coated pure drug bead" by S.M. Lu in "International Journal of Pharmaceutics" vol. 112, Issue 2, 1994, Seiten 117-124.

"Inclusion of ibuprofen in mesoporous templated silica: drug loading and release property" C. Charny et al in" European Journal of Pharmaceutics and Biopharmaceutics", 2004.

"Modelling of drug-release from polydisperse microencapsulated spherical particals" by C. Sirotti et al, 2002, Vo. 19, Seiten 603-614.

"Mesoporous silica: An alternative Diffusion controlled Drug Delivery System, Topics in Multifunctional Biomaterials and Devices" by J. Andersson et al in"Topics in Mulitfunctional Biomaterials and Devices" , 2008.

"Controlled drug delivery system based on ordered mesoporous silica matrices of captopril as angiotensin-converting enzyme inhibitor drug" by R. Popovici et al. In "Journal of Pharmaceutical Sciences" Vo. 100, 2011, Seiten 704-714.

"Tuning drug uptake and release rates through different morphologies and pore diameters of confined mesoporous silica" by V. Cauda et al in "Microporous Mesoporous Mater", 2009, Seiten 435-442.

"3D cubic mesoporous silica microsphere as a carrier for poorly soluble drug carvediol" by Y. Hu et al in" Microporous and Mesoporous Materials", 2012, Seiten 94-101.

"Influences of Material Characteristics on Ibuprofen Drug Loading and Release Profiles from Ordered Micro- and Mesoporous Silica Matrices" by J. Andersson et al in" Chemistry of Materials", vol. 16, Issue 21, 2004, Seiten 4160-4167.

"Mesoporous SBA-15 HPLC evaluation for concentrated gentamicin drug delivery" by A. Doadrio et al in" Journal of Controlled Release", vol. 97, Issue 1, 2004, Seiten 125-132.

"Synthesis of MO-SBA-1 catalyst via sol-gel process and its activity's" by S. Wongkasemijt in" Materials Chemistry and Physics", vol. 117, Issue 1, 2009, Seiten 301-306.

"A detailed Study of Thermal, Hydrothermal and mechanical stabilities of a Wide Range of surfactant assembled mesoporours silicas" by K. Cassiers et al in "Chemistry of Materials", 2002, Seiten 2314-2324.

"Synthesis of highly monodispersed Core/Shell mesoporous silica spheres" by K. Yano et al in" Advances in Science and Technology", vol. 45, 2006, Seiten 814-818.

~"Selective Functionalization of the outer and inner surfaces in Mesoporous Silica Nanoparticles" by J. Kecht et al in "Chemistry Materials", 2008, Band 20, Seiten 7207-7214.

"Facile synthesis of crystal like shape mesoporous silica SBA-16" by J. Jiu et al in" Microporous and Mesoporous Materials", vol. 97, Issues 1-3, 2006, Seiten 141-144.

"Faceted single crystals of mesoporous silica SBA-16 from a ternary surfactant system: surface roughening model" by B. Chen et al in" Microporous and Mesoporous Materials", vol. 81, Issues 1-3, 2005, Seiten 241-249.

"Synthesis of SBA-16 and SBA-15 mesoporous silica crystals template with neutral block copolymer surfactants" by C. Lin et al in"Journal of Physics and Chemistry of Solids" , 2008, Seiten 415-419.

"Hollow cubic shells and assembled porous coatings" by Wan Z et al in" Scripta Materialia", vol. 62, Issue 7, 2010, Seiten 504-507.

"A general PH_responsive supramolecular Nanovalve based on Mesoporous Organosilica Hollow nanospheres" by Wanping Guo et al in " Chemistry—a European Journal"—2010, pp. 8641-8646.

"Hybrid ethan siloxane mesoporous materials with cubic symmetry" by Shiyou Guan et al in" International Symposium on Mesoporous Molecular Sieves", 2001, vol. 44-45, pp. 165-172.

"Humidity sensitive property of Lipoped 3D periodic mesoporous silica SBA-16" by J. Tu et al in"Sensors and actuators. B, Chemical", 2009, vol. 136, No. 2, pp. 392-398.

"Synthesis of mesoporous silica single crystal SBA-16 assisted by fluorinated surfactants with short carbon chains" by X. Meng et al in" Microporous and Mesoporous Materials", vol. 105, Issues 1-2, 2007, pp. 15-23.

"Preparation of highly ordered well-defined single crystal cubic mesoporous silica template by Gemini Surfactant" by Z. Zhang et al in "Chemistry Letters", vol. 31, No. 2, 2003, pp. 584-585.

"Size dependent cytotoxity of monodisperse silica Nanoparticles in Human Endothetical cells" by P. Napierska in "Small", vol. 5, Issue 7, 2009, pp. 846-853.

"Control of Crystal Morphology of SBA-1 Mesoporous Silica" by S. Che et al in "Chemistry Materials", 2001, pp. 2237-2239.

"Morphology and porosity characteristics control of SBA-16 mesoporous silica: Effect of the triblock surfactant Pluronic F 127 degradation during the syntheses" by M. Mesa et al in" Solid State Sciences", vol. 7, Issue 8, 2005, pp. 990-997.

"Nonionic Block Copolymer Synthesis of Large-Pore Cubic Mesoporous Single Crystals by use of Inorganic salts" by C. Yu et al in "Journal of the American Chemical Society", 2002, pp. 4556-4557.

"Recommendations for the characterization of porpus solids" by J. Rouquerol et al in "Pure and Applied Chemistry", Band 66, Heft 8, Seiten 1739-1758 (1994).

M. Valetti-Regi et al, "Mesoporous Materials for Drug Delivery," Angew. Chem. Int. Ed. 2007, 46, 7548-7558 (2007).

"A new property of MCM-41: Drug delivery system " by M. Valetti-Regi et al in" Chemistry of Materials", vol. 13, Issue 2, Seiten 308-311 (2001).

(56) References Cited

OTHER PUBLICATIONS

"Synthesis of core-shell structured Dual-Mesoporous Silica Spheres with Tunable Pore Size and Controllable Shell-Thickness" by D. Niu et al in" J. Am. Chem. Soc.", Seiten 15144-15147 (2010).
"Mesoporous silica Nanoparticles for Drug Delivery and Biosensing Applications" by I. Slowing et al in "Advanced Functional Materials" vol. 17, Issue 8. Seiten 1225-1236 (2007).

"Uniform hollow mesoporous silica nanocages for drug delivery invitro and invivo for liver cancer therapy" by Tingting et al in" Journal of Materials Chemistry", Issue 14, 2011, pp. 5299-5306.
"Microwave synthesis of cubic mesoporous silica SBA-16" by Y. Hwang et al in" Microporous and Mesoporous Materials", vol. 68, Issues 1-3, pp. 21-27 (2004).
"Staeube an Arbeitsplatzen and in der Umwelt" by M. Mattenklott et al in" Gefahrstoffe—Reinhaltung der Luft", pp. 127-129 (2009).

\* cited by examiner

US 9,427,406 B2

SUSTAINED-RELEASE FORMULATION

CROSS-REFERENCE TO RELATED APPLICATIONS

The present application is a continuation-in-part of International Application No. PCT/EP2013/057714 filed on Apr. 12, 2013, which claims priority to British Patent Application No. GB1206547.0 filed on Apr. 13, 2012 and British Patent Application No. GB1220556.3 filed pm Nov. 15, 2012.

The aforementioned applications are hereby incorporated by reference in their entirety.

BACKGROUND OF THE INVENTION

1. Field of the Invention

The present invention discloses a material comprising an assemblage of particles releasing active substances, such as, but not limited to, pharmaceuticals, over a prolonged period of time following a zero order kinetic.

2. Background

The sustained-release of active substances (AS) over long time-scales is a desirable characteristic in many areas such as crop science, medicine, cosmetics, etc. The term "active substance" used in this context denotes any substance that fulfils a specified function. The active substance can be, for example, a biocide, a pharmaceutical, a perfume or flavour, a fertilizer, or a plant hormone. For sustained release, the active substance is dispensed or distributed in a supporting material, so that it slowly dissolves or diffuses into the specified environment. Examples of such formulations are known, for example, from US Patent Application Publication No US 2009/0165515A1, European Patent Application No EP0218148A1 and U.S. Pat. No. 3,994,439.

Sustained-release formulations in medical applications can control rate and period of a drug delivery to a certain degree. It is known that traditional therapies with repeated drug administration result in a saw-tooth curve of drug concentration in the bloodstream. The sustained-release formulations enable keeping the drug concentration in a so-called "therapeutic window" for a prolonged time span. Polymers, such as PLGA (poly-(lactic-co-glycolic acid)) are common carriers for such sustained-release formulations, as described in "Polymeric Delivery Systems for Controlled Drug Release", R. Langer, Chem. Eng. Commun 6 (1980) 1-3, 1. Several modifications of the sustained-release formulation were introduced in order to expand the timescale of the therapeutic window to several weeks or months by reducing diffusion of the active substances. Successful examples of such sustained-release formulations are intercalation of inert nanoparticles (as known from U.S. Pat. No. 6,821,928]) or microencapsulation of the AS (as known from U.S. Pat. No. 6,265,389).

A typical release pattern for slow-release systems is first-order kinetics, in which release rate of the active substance decreases exponentially with time, with relatively high initial release rate. High initial concentrations of some drugs in the bloodstream can cause toxic side effects. After a certain period of time, the concentration of the drug in the bloodstream falls below the necessary therapeutic level [see for a discussion "Nanostructure-mediated drug delivery", G. A. Hughes, Nanomedicine: Nanotechnology, Biology, and Medicine 1 (2005) 22]. In contrast, with a zero-order kinetic release pattern for the active substance a substantially steady therapeutic level can be maintained over the treatment period. This is preferably done with only a single administration of the active substance.

The terms "zero-order release" and "zero-order kinetic" are to be understood in this context as a release pattern of the active substance from a substrate over time, in which the first temporal derivation of the release rate is substantially zero, or, in other words, the release rate remains substantially constant with time. Similarly, the term "first-order release" or "first-order kinetic" is to be understood as a release pattern over time, in which the first temporal derivation of the release rate has a substantially fixed, time-independent value.

In the field of sustained-release formulation, nanoporous materials have drawn much attention as the nanoporous materials are suitable as supporting "host" materials for specific active substances. The ordered nanoporous materials are mainly based on silicon oxide, and, to a lesser extent, on other metal oxides, and comprise a specific oxide with a regular arrangement of pores [see, for example, "Ordered mesoporous materials" U. Ciesla and F. Schueth, Microporous and Mesoporous Materials 27 (1999) 2-3, 131-149].

The term "nanoporous material" (or oxide, silica, etc.) used in this disclosure is to be understood as a porous material with pore diameters substantially between 1 and 100 nm.

The term "mesoporous material" used in this disclosure is to be understood as a nanoporous material with pore diameters substantially between 2 and 50 nm (see J. Rouquerol et al., "Recommendations for the characterization of porous solids (Technical Report)", Pure & Appl. Chem 66 (1994) 8 1739-1758. doi:10.1351/pac199466081739).

The term "monodisperse" as used in this disclosure refers to a collection of particles that are substantially of the same size, shape and mass.

It is known that porous silica ($SiO_2$) is a non-toxic, biocompatible material that can incorporate a high volume of active substances into its open pore system. [regarding the biocompatibility see, for example: "Unique Uptake of Acid-Prepared Mesoporous Spheres by Lung Epithelial and Mesothelioma Cells" S. Blumen et al., American Journal of Respiratory and Molecular Biology vol. 36 (2007), pp. 333-342]. A further advantage of this class of materials, and more particularly, mesoporous ordered silica, is its extreme versatility regarding the shapes and sizes of its pore systems. The pore system can be controlled during the synthesis, thus making various pore sizes and geometries available.

Various structures of the silica materials with different pore geometries are commonly classified by a three-letter code followed by a number. A list of available structures can be found, e.g. in U.S. Pat. No. 7,767,004 B2, Table 1. Additionally, various functional organic groups can be selectively introduced onto the outer and inner surfaces [see "Mesoporous Materials for Drug Delivery", M. Vallet-Regi et al., Angew. Chem. Int. Ed. 46 (2007) 7548].

The sustained release formulations comprise at least two components, namely, the supporting or host material (sometimes called substrate), and the particular active substance. Different superstructures of the two components are therefore imaginable. One superstructure for the sustained release formulation with a zero order kinetic is a "coated pure drug bead", which has a bead exhibiting a core-shell structure. The core is formed by the pure active substance, and the shell is formed by a second, supporting material.

The theoretical release behaviour of such core-shell structures is described in "Dimensionless presentation for drug release from a coated pure drug bead" S. M. Lu, Int. J. of Pharmaceutics 112 (1994), 105-116. It can be derived from this article that a zero-order kinetic sustained release from of a single bead can principally be achieved, if the following three preconditions are fulfilled:

The concentration of the active substance at the border of core to shell remains constant over a prolonged timespan.

The diffusivity of the active substance in the core is much higher than its diffusivity in the shell.

The concentration of the active substance in the surrounding medium of the particle remains zero or negligibly small (perfect sink).

All three preconditions might be, in principal, fulfilled by use of the coated pure drug beads, i.e. the core-shell structure. However, the encapsulation of the pure drug (as the active substance) has disadvantages concerning, for instance, the mechanical stability of core-shell structures during processing. Therefore, a entirely non-collapsible, rigid porous network such as a nanoporous silicate as a supporting material is helpful or often even necessary as, for example, described in US Patent Application No. 2003/175347A1.

The reported results from the coated pure drug beads can be adopted to the more general case of an active substance incorporated into a rigid porous medium. In this latter case, the relevant parameters, for example, the concentration of active substance at the core-shell transition are only weakly altered if the core is highly porous, comprising interconnected channels and an isotropic diffusion behaviour (cubic crystal system), and completely filled with the active substance. Typical examples demonstrate that diffusion of low-molecular substances in the porous systems, and therefore, their elution into the environment are relatively fast and mostly completed within minutes, or, sometimes, hours. [see "*Inclusion of ibuprofen in mesoporous templated silica: drug loading and release property*", C. Charnay et al., European Journal of Pharmaceutics and Biopharmaceutics vol. 57 (2004) 3, pp. 533-540].

In the case of poorly water-soluble active substances, to which belong a vast number of pharmaceutically important substances [see U.S. Pat. No. 6,576,264 B1], all three preconditions outlined above are fulfilled. If the porous core-shell particle is loaded with a poorly water-soluble active substance and brought into an open biological environment, the biological environment will act as a sink for released molecules of the active substance. A steady concentration of the active substance at the core/shell frontier of the particle for a prolonged time can therefore be assumed, since the porous structure will be filled with water from the biological environment. This water acts as a transport medium for the solubilised molecules of the active substance, and keeps the concentration of the active substance at the shell substantially constant. The shell itself must be designed in a way that the shell strongly hinders the diffusion of the active substance.

It would be advantageous to incorporate a large number of the supporting materials in a carrier material, for example, in a polymer extrudate, instead of the preparation of a single large porous particle. The use of the single large porous particle involves the danger of a huge and unwanted overdose of the active substance in case of breaking, and, therefore, of uncontrolled fast release from this single large porous particle. In contrast, in case of the breakage of the polymer extrudate containing a large number of small particles, only a small fraction of the particles would be destroyed, and the amount of the active substance released would be much smaller. For medical applications, the use of such an assemblage of particles is therefore preferable.

In other applications, for example, in crop science, a wide-area application of the small particles as individual reservoirs for the active substances is additionally advantageous in order to achieve a substantially constant concentration of the active substance (e.g. biocides) in time and space. This allows a reduction of the total amount of the active substance per area unit, since any unnecessary local overdose in area or time can be avoided. Other examples may comprise glues, coatings and lacquers, in which the particles releasing, for example, a biocide can be incorporated and prevent the particular composition from fouling.

To ensure that such desirable release kinetics from a single particle can be transferred to an assemblage of particles, the size distribution of the particles in the assemblage must be substantially monodisperse and show only a small standard deviation.

This requirement is shown, for example, in "*Modelling of drug-release from poly-disperse microencapsulated spherical particles*", C. Sirotti et al., J. Microencapsulation, 19 (2002) 5, 603-614. It can be even more clearly visualized if for each particle of a batch a perfect zero order kinetic is assumed, i.e. a constant release of the active substance over time until the reservoir (core) is emptied, followed by a sudden and abrupt stop.

The amount of the active substance incorporated into the particle is directly proportional to the volume of the core of the particle, which is related to the cube of the particle radius. The amount of released active substance per unit time is related directly to the surface area of the particle, which is the square of the particle's radius multiplied by $4\pi$. Thus, not only the standard deviation (SDV) of the size of the core-depot, but also the SDV of the amount of the active substance released per time is strongly affected by the SDV of the particle's diameter. For example, the volumes of the smallest particles (2 micrometers in diameter) and the biggest particles (2.5 micrometers in diameter) in a mixture (that corresponds in this case to 11.1% deviation from a mean particle size of 2.25 micrometers) differ almost by the factor of two. It is thus obvious, that a broad size distribution of the particles results in a huge, undesired distortion of the aimed zero-order kinetics. Hence, the particle size distribution has to be as sharp as possible.

The correlation, visualizing quantitatively the effect of a different SDV for assemblies of the particles, can be derived as follows (if a large core and a negligible thin shell is assumed, so that $r_{core} \approx r_{core}+r_{shell}$, where $r_{core}$ is the radius of the core and $r_{shell}$ is the radius of the shell).

The amount of incorporated substance is assumed to be directly proportional to the available volume of the depot, hence the mass of incorporated AS is $$m=c_1 4/3 r^3 = c_2 r^3 \qquad \text{Eq. 1}$$

The amount of the active substance released per time is proportional to the surface of one particle $$\frac{dm}{dt} = c_3 4\pi r^2 = c_4 r^2 \qquad \text{Eq. 2}$$

Separation and integration of Eq. 2 leads to $$\int dm = \int_0^t c_4 r^2 dt \qquad \text{Eq. 3}$$

$$m = c_4 r^2 t \qquad \text{Eq. 4}$$

Combination with Eq. 1 results in $$\frac{c_2}{c_4}r = c_5 r = t \qquad \text{Eq. 5}$$

The Eq. 5 shows the time at which the core depot of the particle is emptied. It is linearly related to the radius of the particle and dependent on the diffusion rate of the active substance through the shell, which correlates with constant $c_3$ and, therefore, $c_4$.

Since the standard deviation and its influence on the release properties is the most interesting, constants $c_2$, $c_4$ and $c_5$ in this example are defined to be equal to 1.

The size distribution of the particles is given by the Gaussian distribution $$P(r) = \frac{1}{\sigma\sqrt{2\pi}} \exp\left(-\frac{1}{2}\left(\frac{r-\mu}{\sigma}\right)^2\right) \qquad \text{Eq. 6}$$

where r is the particle radius, $\mu$ is the mean radius, $\sigma$ is the standard deviation.

The amount of the active substance released by all the particles per time is given by the sum, and, hence, by the integral of P(t), multiplied by the surface area of the particles.

$$\frac{dm}{dt}\frac{1}{m} = \frac{\int_{r(t)}^{\infty} c_4 r^2 \frac{1}{\sigma\sqrt{2\pi}} \exp\left(-\frac{1}{2}\left(\frac{r-\mu}{\sigma}\right)^2\right) dr}{\int_0^{\infty} c_2 r^3 \frac{1}{\sigma\sqrt{2\pi}} \exp\left(-\frac{1}{2}\left(\frac{r-\mu}{\sigma}\right)^2\right) dr} \qquad \text{Eq. 7}$$

The denominator reflects the overall amount of the active substance, to normalize the curves obtained for different standard deviations and mean particle sizes. To calculate the release rate at a given time, the starting point of the integral of the nominator has first to be found from Eq. 5. The result is a value for a radius, corresponding to the sizes of the particles that no longer contain the active substance at a time t. Hence, the integration is done for all the particles that still contain active substance. The amount of the particles inside a given dr is multiplied by $c_4 r^2$, which gives the release rate (Eq. 2).

FIG. 16 shows four different curves relating to four different standard deviations. It can be clearly seen, that a relatively large SDV leads to a distorted release curve, in comparison to an almost rectangular curve for SDVs that are smaller than 10% of the mean particle size.

Prior Art

The use of nanoporous and mesoporous silica materials in sustained-release systems has been extensively discussed in literature. However, the known materials and formulations have been shown to have disadvantages limiting their use as a host for active substances in sustained-release applications.

The literature on attempts to use these nanoporous and mesoporous silica materials as the hosts for sustained-release applications can be divided into two major groups. The first group comprises rather simple approaches in which a potentially surface-modified host is loaded with the active substance. An overview of this approach can be found in "*Mesoporous Silica: An Alternative Diffusion Controlled Drug Delivery System, Topics in Multifunctional Biomaterials and Devices*"; J. Andersson et al., Ashammakhi, N., Ed.; E-book, (2008).

Example are also disclosed in:

"*Inclusion of ibuprofen in mesoporous templated silica: drug loading and release property*", C. Charnay et al., European Journal of Pharmaceutics and Biopharmaceutics 57 (2004), 3, 533-540;

"*Controlled Drug Delivery System Based on Ordered Mesoporous Silica Matrices of Captopril as Angiotensin-Converting Enzyme Inhibitor Drug*", R. Popovici et al., Journal of Pharmaceutical Sciences 100 (2011), 2, 704-713;

"*Tuning drug uptake and release rates through different morphologies and pore diameters of confined mesoporous silica*" V. Cauda et al., Microporous and Mesoporous Materials 118 (2009) 435-442;

"*3D cubic mesoporous silica microsphere as a carrier for poorly soluble drug carvedilol*" Y. Hu et al., Microporous and Mesoporous Materials 147 (2012), 94-101.

Even though these nanoporous and mesoporous silica materials loaded with the active substance exhibit a retarded release kinetic, leaching of the active substance is still too fast, as the leaching is based solely on the diffusion retardation inside the nanoporous host channels of individual nanoporous and mesoporous silica particles. Most of the active substances are eluted typically from the nanoporous and mesoporous silica particles after several hours. This rapid elution indicates that it is not possible to realize a zero-order kinetic in the range of days, and certainly not in terms of weeks or months in such a basic system.

The release time and the kinetics can be improved if moulded paddings with dimensions of several mm are prepared from the individual nanoporous and mesoporous silica particles, as, for example, disclosed in "*A New Property of MCM-41: Drug Delivery System*" M. Vallet-Regi et al., Chemistry of Materials 13 (2001), 308-311;

"*Influences of Material Characteristics on Ibuprofen Drug Loading and Release Profiles from Ordered Micro-and Mesoporous Silica Matrices*", J. Andersson et al, Chem. Mater 16 (2004) 4160-4167

"*Mesoporous SBA-15 HPLC evaluation for controlled gentamicin drug delivery*", A. Doadrio et al., Journal of Controlled Release 97 (2004), 125-132.

However, in that case, the main advantage of a particle assemblage of the nanoporous and mesoporous silica particles, namely, the possibility of achieving a homogenous release of the particular active substance in space by a distribution of the nanoporous and mesoporous silica particles in a particular environment is lost.

The second group of materials comprises core-shell materials, in which more efficient release retardation is achieved by adding a shell that hinders the leaching of the active substance out of the reservoir core, as described in the theoretical section above. However, zero order kinetics of the active substance release over a period longer than 1 day could not be observed with the previously disclosed systems.

One reason for the lack of zero order kinetics might be the insufficient average size of the nanoporous and mesoporous silica particles used, which are in the range of several hundred nanometers, as disclosed in "Synthesis of Core-Shell Structured Dual-Mesoporous Silica Spheres with Tunable Pore Size and Controllable Shell Thickness", D. Niu et al, Journal of the American Chemical Society 132 (2010), 15144-15147, and thus a too small reservoir size.

In "*Mesoporous Silica Nanoparticles for Drug Delivery and Biosensing Applications*", I. Slowing et al., Advanced Functional Materials vol. 17 (2007), p. 1225, the synthesis of monodisperse separate mesoporous silica core-shell nanoparticles for a controlled-release of drugs as the active substance is described. However, in these kinds of materials the shell consists of polymers, e.g. polylactides, and is not an entirely ordered mesoporous structure based on silicon oxide. It is obvious that these kinds of materials do not exhibit the same mechanical rigidness as materials based on an inorganic oxide framework. Since this work (partially described in U.S. Pat. No. 7,563,451B2) is mainly focused on targeted delivery of drugs inside a human body and not on mere time-dependent release, there are no examples of a sustained release of a particular one of the active substance given. It is doubtful that a release over a timespan exceeding several days can be realized with the materials disclosed therein, because the maximal particle diameter of several hundreds of nanometers, and hence the reservoir size is simply too small.

A system built of a porous rigid core and polymer shell is also described in US Patent Publication No. US2009/0304756A1, Daehne et al. The polymeric shell is in particular adapted for a triggered release of encapsulated ingredients by removing the encapsulated ingredients, for example by mechanical stress (see paragraphs [0062] and [0067] in US2009/0304756A1, Daehne et al.). Thus, in formulations which are made for the sustained release of encapsulated ingredients only, a sensitivity to mechanical stress resulting in an unwanted burst in the release ingredients is undesirable.

Another example for such a material exhibiting a mesoporous core and a pure polymer shell can be found in US Patent Application Publication No. US2006/0018966A1, Lin et al. Paragraph [0110] on page 13 describes in detail how the porous core is coated by a pure polymer shell, in this case made from a polylactic acid.

International Patent Application No. WO2005/009602 is related to the aforementioned US7563451B2, Lin et al. and teaches further the synthesis of a variety of mesoporous silica particles. The use of the synthesised mesoporous particles in different applications is described in detail. All materials disclosed are however related to a material named MCM-41, which exhibits a hexagonal 2-D structure, e.g a hexagonal symmetry, consisting of isolated, non interconnected cylindrical channels (see page 27 line 30-32, page 50 line 27-29, page 51 line 3 and line 10-12, page 56 line 15-23, page 61 line 21-23,) or disordered, wormlike structures, also related to material MCM-41, with cylindrical pores (page 51 line 6-8, page 56 line 15-23, page 63 line 20-21). Thus, diffusion behaviour of encapsulated substances in this mesoporous silica particle cannot be regarded as isotropic. None of the mesoporous silica particles disclosed in WO2005/009602, Lin et al. show a cubic crystal symmetry with a highly interconnected channel system nor do the mesoporous silica particles comprise a superimposed core-shell structure. The particle assemblages taught in this document fail to exhibit a standard deviation suitable for the aimed application described in this disclosure. The standard deviation of particles can be deduced exemplarily from SEM-Picture No. 17D, 17F, and was determined to 7.6+−2.4 µm (31.6%) in 17D and 8.25+−3.58 (43.6%) in 17F.

The mesoporous silica materials of WO '602 differ also in respect to the mean particle size and alkaline synthesis medium in contrast to the acidic synthesis medium disclosed in this current disclosure. The difference in synthesis conditions might influence the polymerization degree of the obtained silicate ("A detailed Study of Thermal, Hydrothermal, and mechanical Stabilities of a Wide Range of Surfactant Assembled Mesoporous Silicas", K. Cassiers et al, Chem. Mater. 2002, 14, 2317) and thus also influence the stability, especially the hydrothermal/thermal stability. The inventors of the current disclosure understand that it is preferable to choose an acidic environment for the synthesis of particles. The crystal facets visible in the particles of the current disclosure might be the underlying result of such a better and stronger degree of polymerisation.

Related to the inventions described in the patent documents Nos. WO2005/009602 and US7563451B2 is US Patent Publication No. US2006/0018966A1, Lin et al. In this invention a series of mesoporous particle assemblages based on silicon dioxide is disclosed for use in different release formulations. However, none of the mesoporous particle materials out of the whole series of materials disclosed in US '966 exhibits a cubic symmetry. On the contrary the materials disclosed in US '966 exhibit hexagonal MCM-41 type symmetries, chiral twisted hexagonal symmetry or were disordered (0076 to 0078 on pages 9-10, see also XRD Pattern in FIG. 4) clearly related to hexagonal structures. As in WO2005/009602 only basic media were used to prepare all of the materials and no crystal facets were observed.

In WO2009/010945A2, Holmes et al, monodisperse assemblages of mesoporous particles based on silicon oxide are disclosed. The disclosed method of preparation differs however from the method of this disclosure, resulting in different materials. In WO2009/010945A3 only basic media, in particular ammonia containing media are used for synthesis. This results in particle morphologies similar to the ones of WO2005/009602, Lin et al, but very different to the materials of this disclosure. For example, particles are by definition of WO2009/010945A2 (page 10 line 25-26, see also claim 69) a sphere, rod, disc or rope, but not a decaoctahedron with clearly separated facets, as taught in this disclosure. The arrangement of channels is described as being ordered in a random direction (page 9 line 27-29, page 10 line 19-20, claim 68), which excludes materials with an entirely cubic symmetry. A material with a cubic symmetry is not disclosed in WO2009/010945A2.

There are several other publications describing the synthesis of mesoporous core-shell materials. However, these publications do not disclose materials that are explicitly used for sustained-release or targeted-release formulations, or the materials disclosed there are for various reasons not suitable for the aimed applications within the framework of this invention.

Entirely mesoporous core/shell particles are described in "Synthesis of Highly Monodispersed Core/Shell Mesoporous Silica Spheres" K. Yano et al., Chemistry Letters vol. 35 (2006), 9, p. 1014, in Japanese Patent Application Abstract No JP 2006 347849A, and in "Selective Functionalization of the Outer and Inner Surfaces in Mesoporous Silica Nanoparticles", J. Kecht et al., Chemistry of Materials 20 (2008) 7207. All of the materials disclosed in the publications of K. Yano and J. Kecht possess a radially aligned pore structure of 1D channels of different length and show non-faceted materials. As the channels are not interconnected in all spatial directions, each channel can be considered as an individual depot containing unequal amounts of the active substance, which leads to undesirable release rate fluctuations in time.

Furthermore, JP 2006347849A says in paragraph [0040] that a silica raw material is made to react in a basic solvent, since in acidic environments the reaction hardly advances. This is an observation which is contrary to the teachings of the current disclosure. The results also differ. The materials disclosed in JP 2006347849A are non faceted spheres, and not one of the disclosed synthesised materials exhibits a cubic symmetry. Instead it is said in paragraphs [0020] related to [0019] that materials show a hexagonal diffraction pattern.

Mesoporous materials with an interconnected channel system in all three spatial dimensions are known and described in a number of examples in literature. An overview of different types of such materials can be found, for example, in U.S. Pat. No. 7,767,004 B2.

However, the previously described materials possess at least one major disadvantage when employed as a host material for the aimed application.

A first major disadvantage of most of the previously described materials is the large deviation of particle size within a batch, which is not easy to overcome. This strongly limits the use of these materials as a host system. Table 1 shows some materials and their standard deviation in particle size, as well as other properties. The standard deviations were derived from disclosed SEM-pictures by counting the particles and measuring their diameter.

A second major disadvantage of many of the previously described materials is severe particle aggregation that often takes place in this specified class of materials (the term "aggregation" herein is to be understood as defined by the German DIN Standard No. 53 206). The existence of separate, non-aggregated particles is a precondition for a complete, homogenous and uniform epitaxial coating of every single particle. Thus, aggregation and subsequent intergrowth is clearly to be avoided if the material is supposed to be used as a host for the aimed purposes.

The use of bridged siloxanes in hybrid mesoporous materials, as taught in "*Hybrid ethane-siloxane mesoporous materials with cubic symmetry*", Microporous and Mesoporous Materials 44-45 (2001) 165 seems to allow the synthesis of particles with a sharper size distribution, as it is shown on the disclosed SEM micrographs. Beside the limited diversity and unknown biocompatibility of these materials, the price of bridged siloxanes, necessary for making this type of materials, is about 20 times higher than that of typically used starting compounds such as tetraethoxysilane. This leads to extremely high, often inacceptable costs of the end product.

TABLE 1

| Number | Publication | Aggregates | Size ± standard deviation | SDV/Meansize * 100% |
|---|---|---|---|---|
| 1 | "*Facile synthesis of crystal like shape mesoporous silica SBA-16*" J. Jin et al. Microporous and Mesoporous Materials vol. 97 (2006), pp. 141-144 | Yes | — | — |
| 2 | "*Faceted single crystals of mesoporous silica SBA-16 from a ternary surfactant system: surface roughening model*" B. Chen et al., Microporous and Meso-porous Materials vol. 81 (2005) pp. 241-249 | No | 4.0 ± 1.3 µm | 32.5% |
| 3 | "*Synthesis of SBA-16 and SBA-15 mesoporous silica crystals templated with neutral block copolymer surfactants*" C. Lin et al. Journal of Physics and Chemistry of Solids vol. 69 (2008), pp. 415-419 | No | 3.9 ± 1.1 µm | 28.2% |
| 4 | "*Humidity sensitive property of Li-doped 3D periodic mesoporous silica SBA-16*" J. Tu et al. Sensors and Actuators B vol. 136 (2009) pp. 392-398 | No | 1.2 ± 0.4 µm | 33.3% |
| 5 | "*Synthesis of mesoporous silica single crystal SBA-16 assisted by fluorinated surfactants with short carbon-chains*" X. Meng et al., Micro-porous and Mesoporous Materials vol. 105 (2007) pp. 15-23 | Some | 2.56 ± 1.07 µm | 41.7% |
| 6 | "*Microwave synthesis of cubic mesoporous silica SBA-16*" Y. Hwang et al. Microporous and Mesoporous Materials vol. 68 (2004) pp. 21-27 | Yes | — | — |
| 7 | "*Preparation of Highly Ordered Well-defined Single Crystal Cubic Mesoporous Silica Templated by Gemini Surfactant*" Z. Zhang et al. Chemistry Letters (2002) pp. 584-585 | No | 6.52 ± 1.13 | 17.3% |

SUMMARY OF THE INVENTION

A substantially monodisperse assemblage of particles having interconnected nanosized pores and a nanoporous core with at least one shell disposed about the core and wherein the particles have a cubic crystal form with facets and wherein the nanosized pores have a diameter between 1 and 100 nm is disclosed.

The assemblage of particles may have at least two shells disposed about the core.

The elementary composition of the particles may comprise at least 90% of materials selected from the group consisting of metal oxides and metalloid oxides.

In one aspect of the disclosure, the elementary composition of the particles may comprise 95% of materials selected from the group consisting of metal oxides and metalloid oxides.

In another aspect of the disclosure, the material is silicon oxide.

The average particle size of the particles may be greater than 1 micrometer.

In one aspect of the disclosure, the average particle size of the particles is greater than 2 micrometers.

In another aspect of the disclosure, the average particle size of the particles is greater than 6 micrometers.

The standard deviation of the particle size may be less than 15% of the average particle size.

In one aspect of the disclosure, the standard deviation of the particle size is less than 10% of the average particle size.

The interconnected nanosized pores of the at least one shell may comprise restrictions by covalent bonds between a molecule and the nanosized pore.

The restrictions may comprise at least one of organic molecules or polymers covalently bound to an inner surface of the interconnected nanosized pores of the at least one shell.

In one aspect of the disclosure, the restrictions comprise dextran or a derivative thereof.

The assemblage of particles may further comprise an active substance in at least some of the interconnected nanosized pores of the core.

A method for the sustained release of an active substance to an environment is disclosed, the method comprising:
  adding the active substance to a substantially monodisperse assemblage of particles having interconnected nanosized pores and a nanoporous core with at least one shell disposed about the core, wherein the particles have a cubic crystal form with facets and wherein the nanosized pores have a diameter between 1 and 100 nm;
  placing restrictions in the interconnected nanosized pores within the shell by covalent bonding; and
  placing the substantially monodisperse assemblage of particles with the added active substance in the environment.

The active substance may be an active pharmaceutical ingredient.

A method for the manufacture of a substantially monodisperse assemblage of particles having interconnected nanosized pores and a nanoporous core with at least one shell disposed about the core and wherein the particles have a cubic crystal form with facets and wherein the nanosized pores have a diameter between 1 and 100 nm is disclosed, the method comprising:
  mixing an ionic surfactant with an inorganic salt in hydrochloric acid;
  mixing a co-solvent with a first non-ionic surfactant and a first oxide source;
  mixing the solution of the ionic surfactant and the inorganic salt with the solution of the first non-ionic surfactant and the first silicon source in the first co-solvent.

The oxide source may be a silane.

The co-solvent may be selected from the group consisting of dimethyl acetamide, N,N-dimethylformamide, 1,3-dimethyl-3,4,5,6-tetrahydro-2(1H)-pyrimidinone, dimethyl sulfoxide, N-methyl-2-pyrrolidone.

The non-ionic surfactant may be a polyalkyleneoxide.

The method for the manufacture may further comprise:
  mixing a second co-solvent with a second non-ionic surfactant and a second silicon source;
  adding after a period of time the solution of the second co-solvent with the second non-ionic surfactant and the second silicon source to the solution of the ionic surfactant and the inorganic salt and the first non-ionic surfactant and the first silicon source in the first co-solvent.

The method for the manufacture may further comprise functionalising inner walls of at least some of the nanosized pores in the monodisperse particles.

In another aspect of the disclosure, the method for the manufacture further comprises adding an active substance to the monodisperse particles.

The method for the manufacture may further comprise attaching restrictions to the functionalised inner walls by covalent bonding.

The restrictions may be formed of dextran polymers or derivatives thereof.

DETAILED DESCRIPTION OF THE INVENTION

Figure 1:
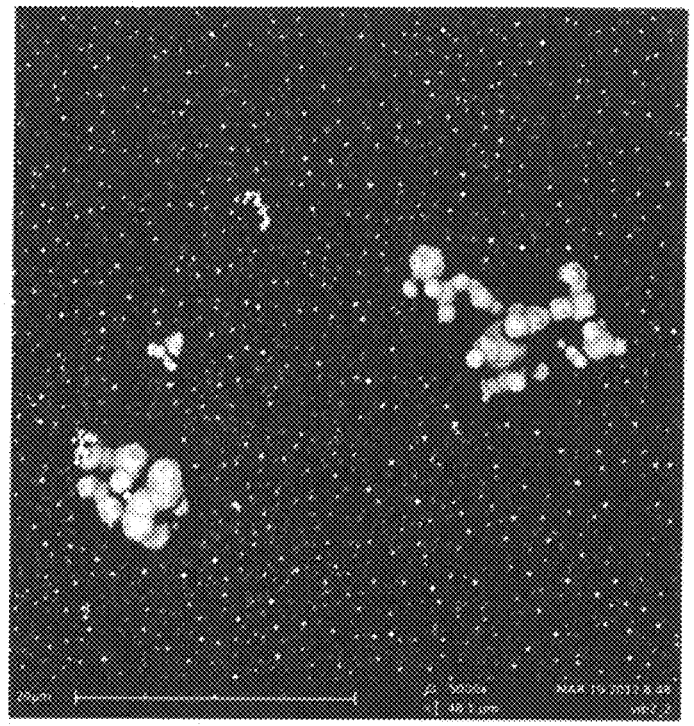
FIGS. 1 to 7m depict representative SEM images corresponding to the examples given in Table 2.
Figure 2:
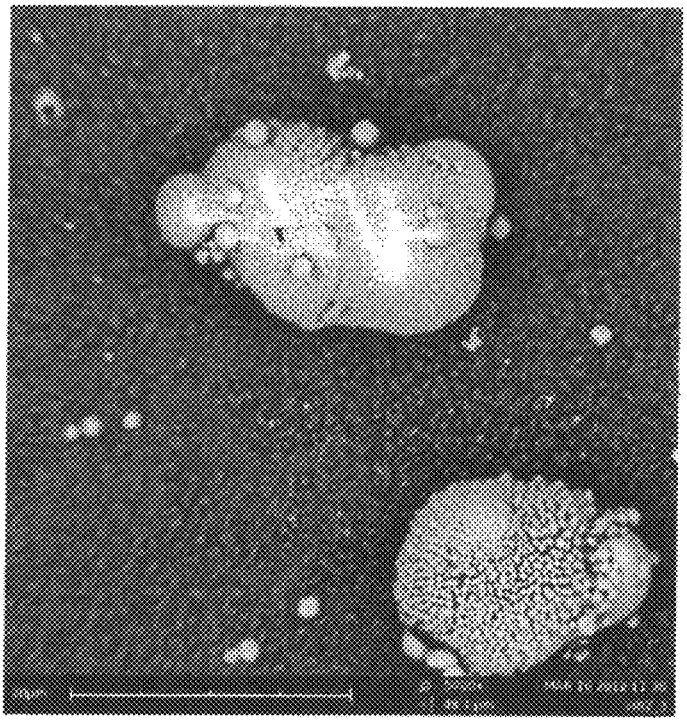
Figure 3:
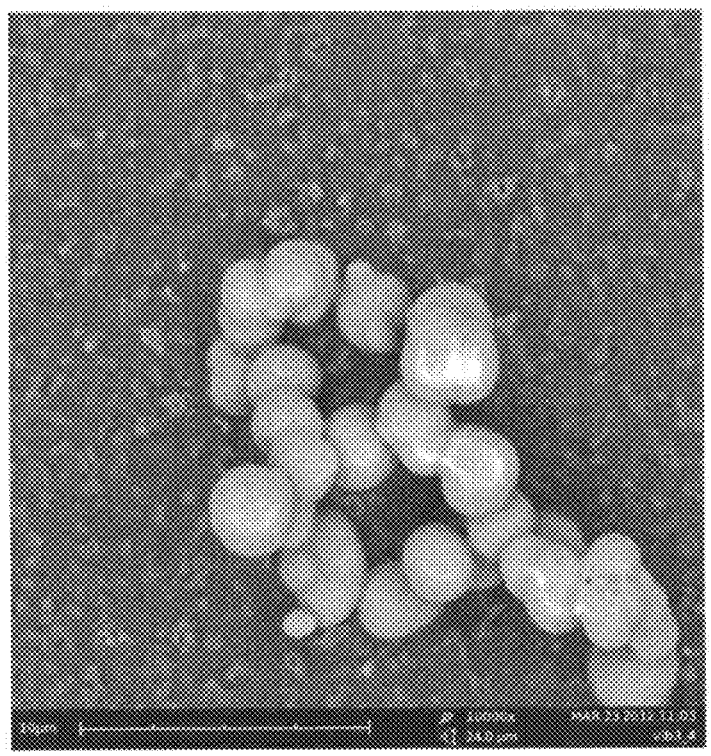
Figure 4:
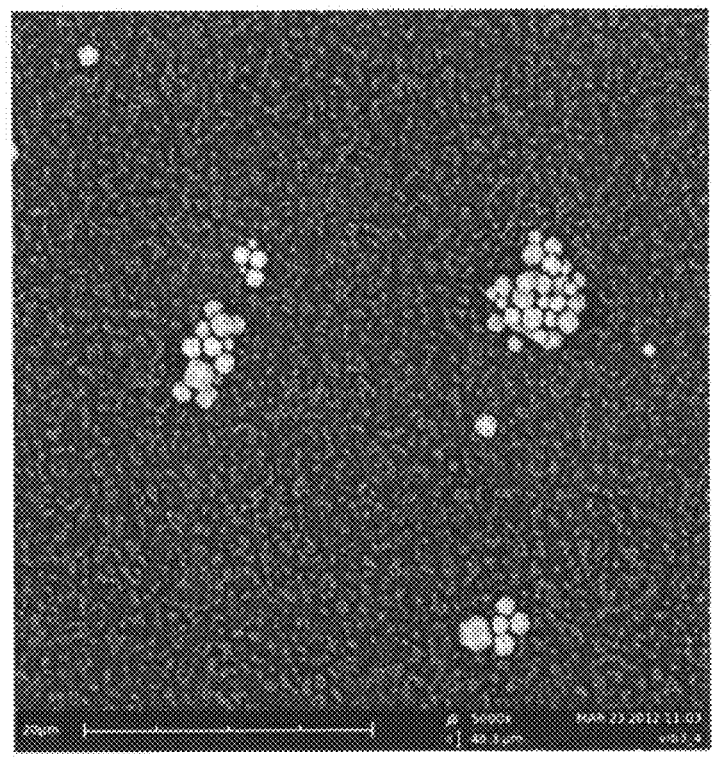
Figure 5:
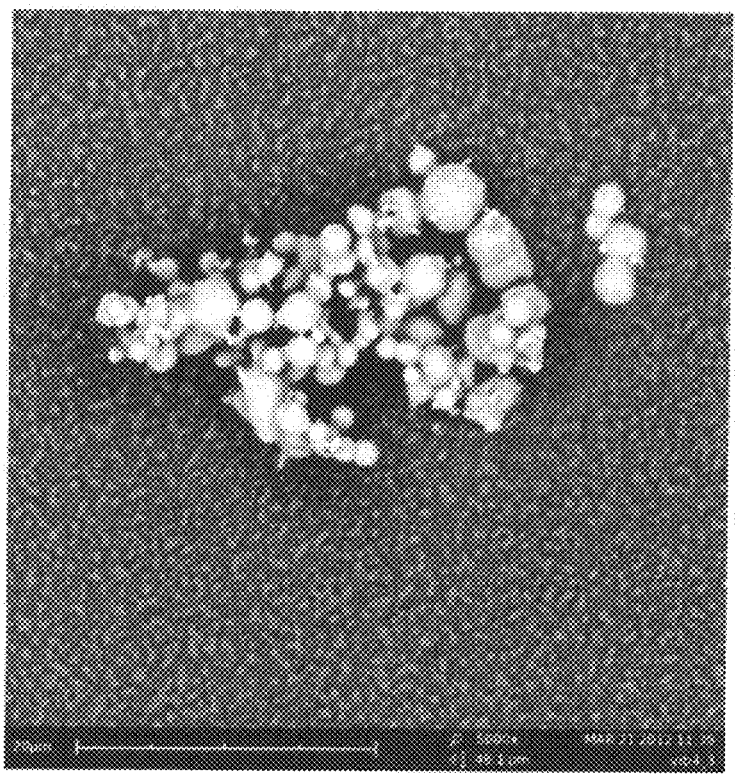
Figure 6:
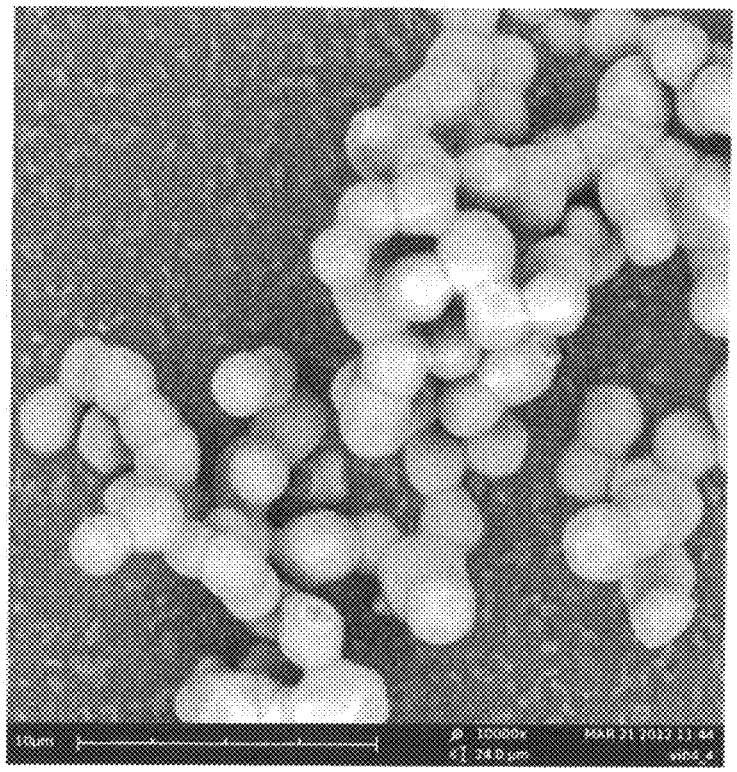
Figure 7A:
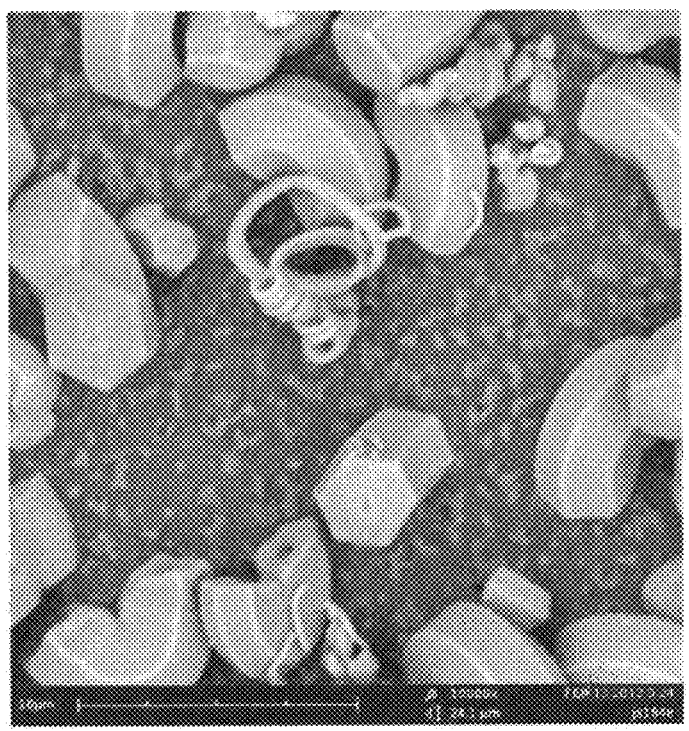
Figure 7B:
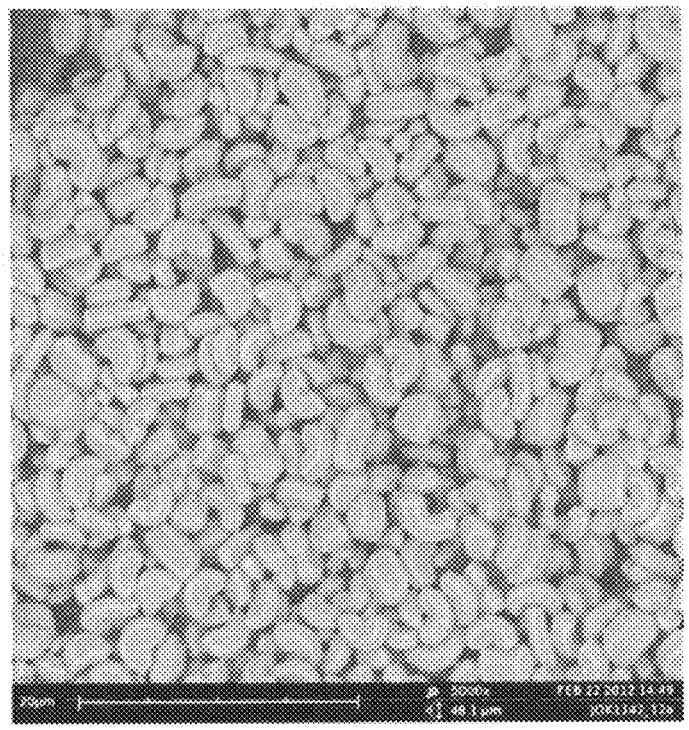
Figure 7C:
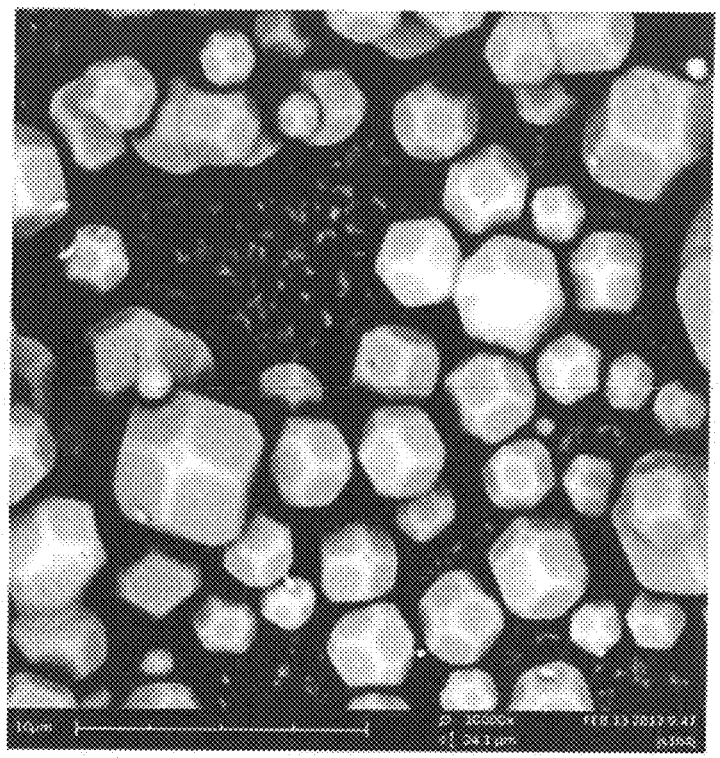
Figure 7D:
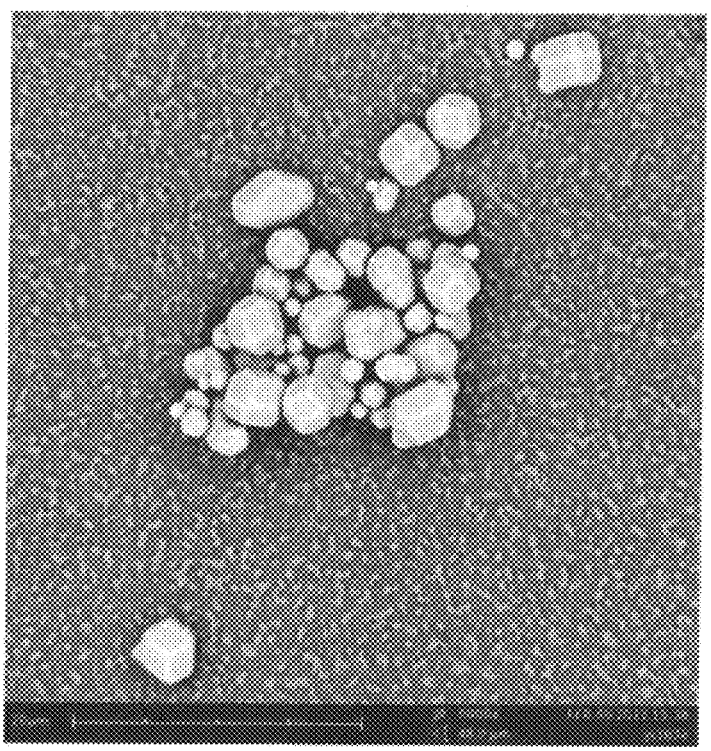
Figure 7E:
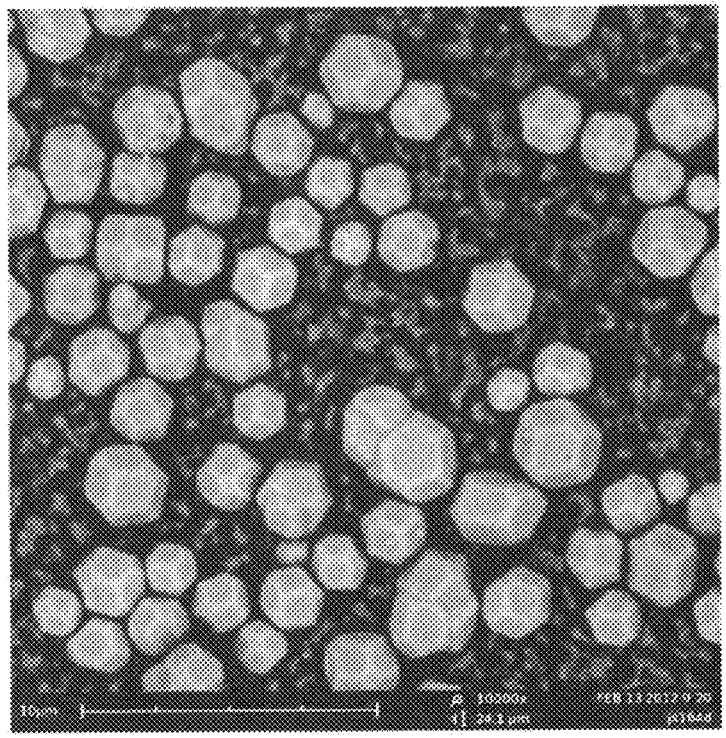
Figure 7F:
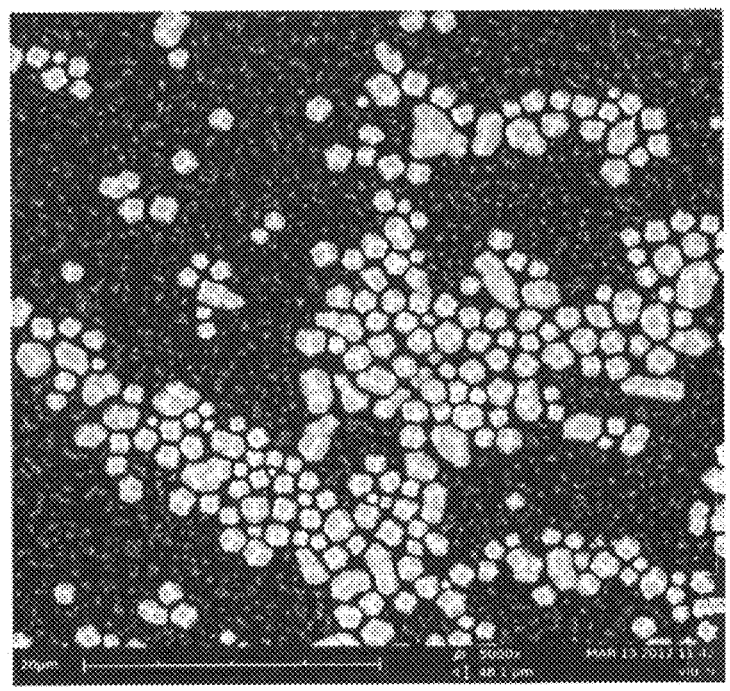
Figure 7G:
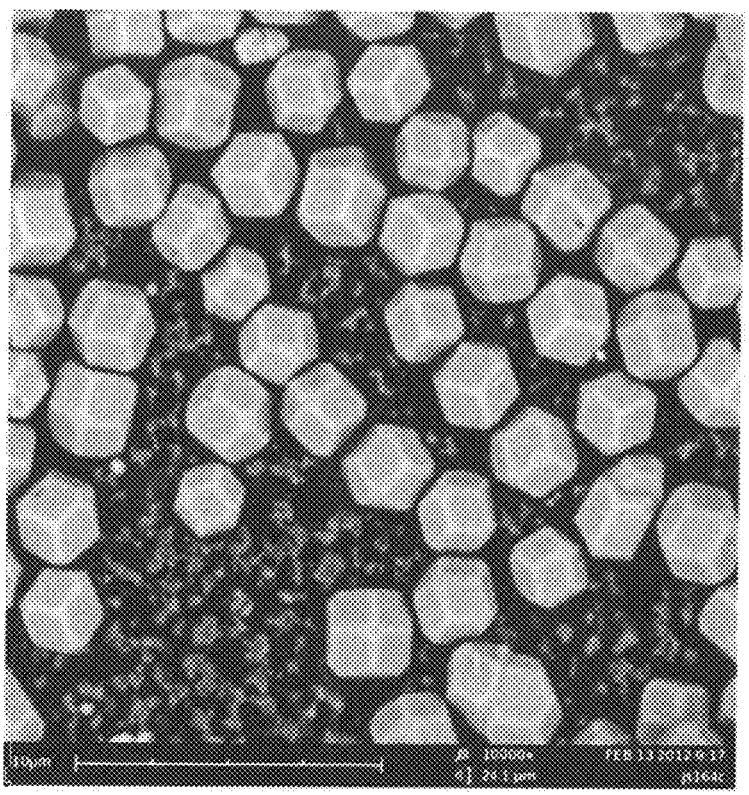
Figure 7H:
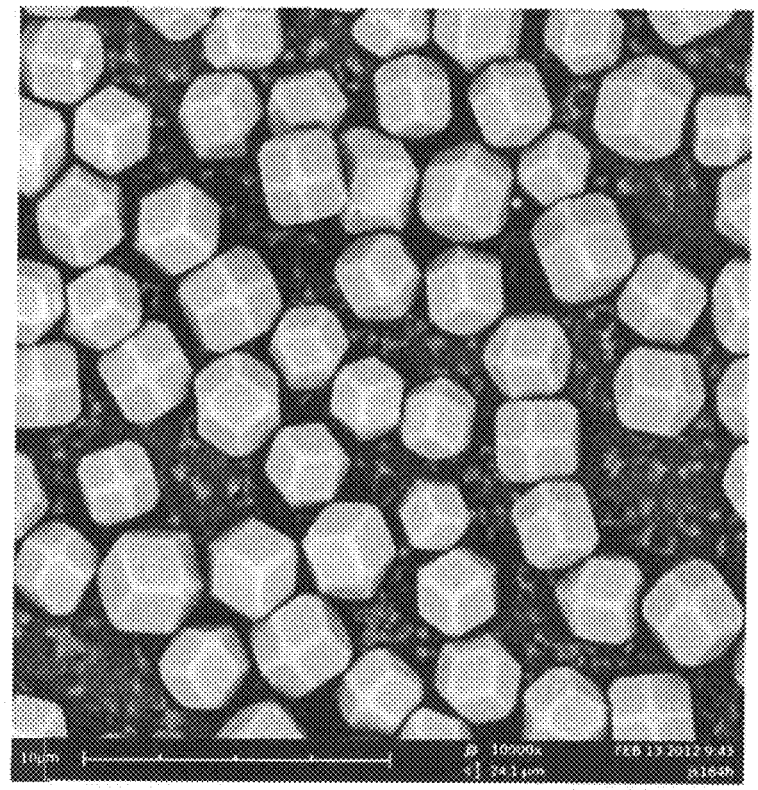
Figure 7I:
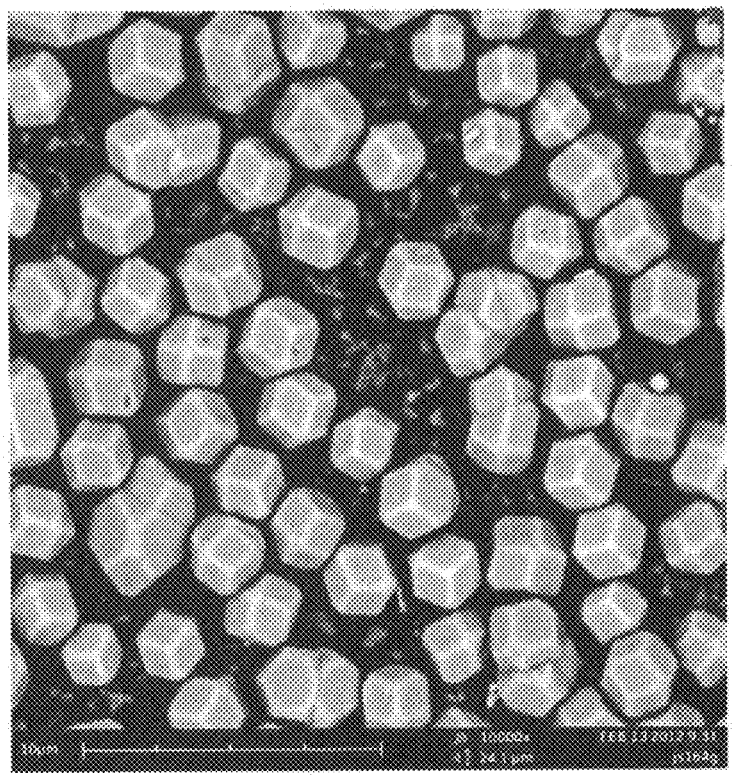
Figure 7J:
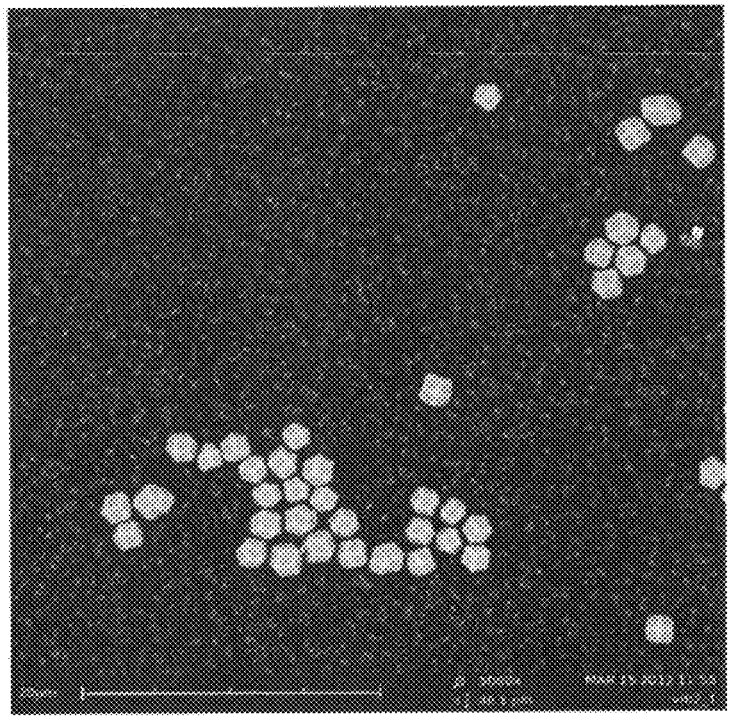
Figure 7K:
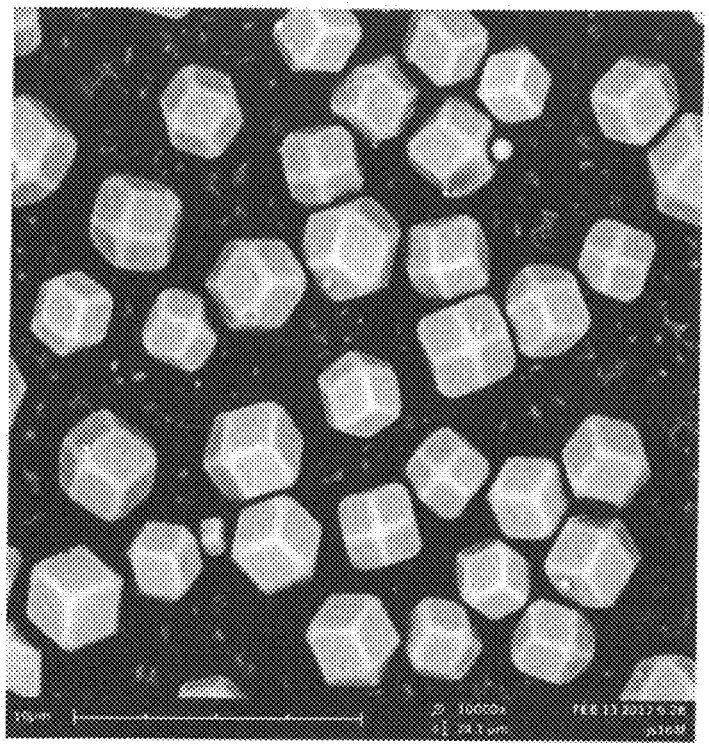
Figure 7L:
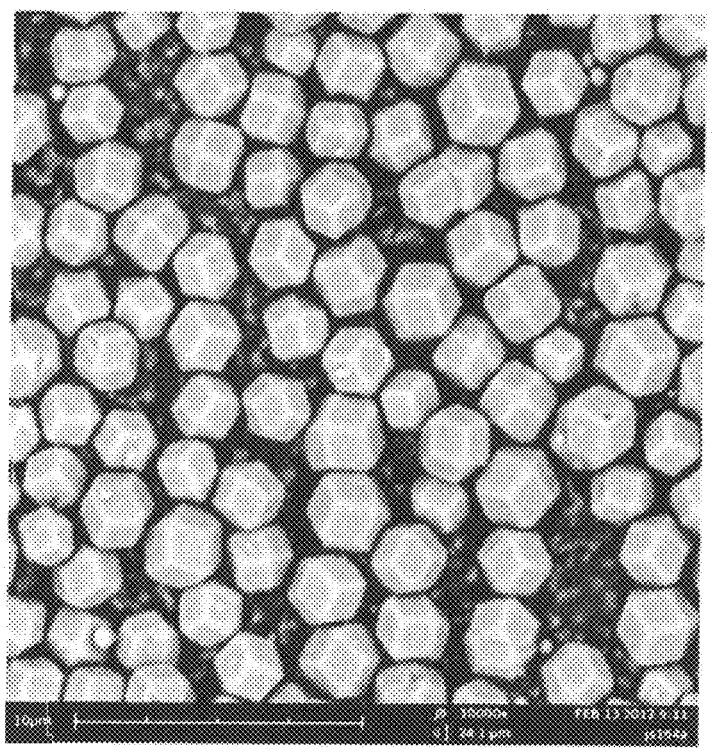
Figure 7M:
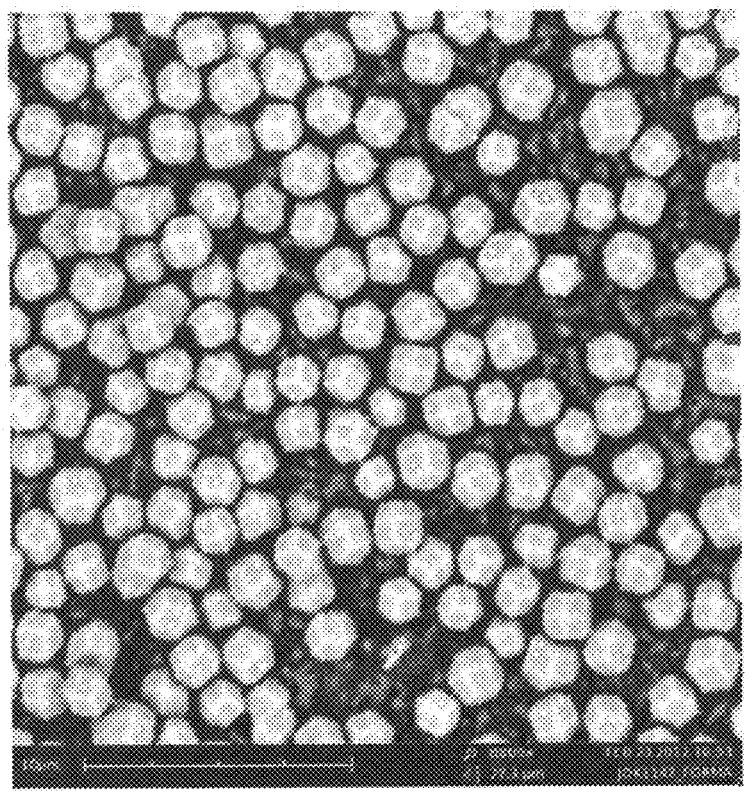

The invention will now be described on the basis of the drawings. It will be understood that the embodiments and aspects of the invention described herein are only examples and do not limit the protective scope of the claims in any way. The invention is defined by the claims and their equivalents. It will be understood that features of one aspect or embodiment of the invention can be combined with a feature of a different aspect or aspects and/or embodiments of the invention.

The introduction to the application outlined a theoretical approach that serves as the basis for the invention. A practical approach involved possession of monodisperse nanoporous particles. The use of nanoporous, and especially mesoporous silica as a rigid, porous matrix for the applications is demonstrated. It is believed that cubic mesoporous materials are suitable for the application, because diffusivity in such cubic mesoporous materials is substantially isotropic and is not hindered in one or two dimensions, unlike the case of the hexagonal materials, for example, SBA-15 or MCM-41 mesoporous silica.

The use of a monodisperse assemblage of cubic mesoporous core-shell particles with small size deviations allows in principle the realization of formulations with the desired release kinetics. The release kinetics can follow a zero-order pattern, if the diffusivity in the core of the core-shell particle is much higher than in the shell. It is found that the diffusivity can be tuned by different chemical modifications of the pores in the core and especially in the shell.

For many applications, relatively large particles with diameters above 1 µm are desirable. A small size of the particles in a range of up to several hundred nanometers is necessary and advantageous, when the particles are supposed to interact with, or travel through, a biological system, for example, a human body. However, the use of such small-sized materials as an inert passive depot for a sustained-release formulation is, in contemporary medical opinion, connected with an increased risk of cytotoxicity of nanoparticles, especially those with a small size, as a result of their increased ability to penetrate cells. This is discussed in "*Size-Dependent Cytotoxicity of Monodisperse Silica Nanoparticles in Human Endothelial Cells*", D. Napierska, Small vol. 5 (2009) 7, p. 846. It has also been reasoned that the high surface area-to-mass ratio could be an important parameter in the toxicity of the nanoparticles. Thus, contemporary opinion suggests that the medical use of particles of <1 micrometer diameter for medical applications represents significant health risks.

A further consideration is that, if a sustained-release formulation is supposed to be distributed in the environment as, e. g., a delivery depot for biocides, particles in the nanometer range should be avoided. A particle size of 2 micrometers or more is much more advantageous, because the increase of a particle size leads to a bigger reservoir capacity and thus to a prolonged timespan for the release of the specific active substance.

Larger particles are also less amenable to the accumulation by lung alveoli. For example, particles with a diameter of 2 µm are alveolar to a fraction of more than 90%, whilst particles with a diameter of 7 µm to less than 10%, as discussed in "*Staeube an Arbeitsplaetzen und in der Umwelt*", M. Mattenklott et al, Staeube an Arbeitsplaetzen und in der Luft_Gefahrstoffe-Reinhaltung der Luft_vol. 69_(2009) 4 (Apr.) p. 127; Springer-VDI-Verlag, Duesseldorf.

This disclosure discusses the necessary host material and its modifications in order to achieve large differences in the diffusivity inside the core versus the shell and, therefore, to enable the use of the host material in sustained-release formulations for the active substances.

The method offers the possibility of preparing core-shell particles possessing several shells, each of which may be different in chemical compositions. The use of such core and multi-shell particles can be advantageous, if a number of the particle's properties is desirable. Different chemical functionalities inside the particles can be used, for example, for the creation of inner diffusion-hindering layers, for making layer(s) providing a chemical modification of a released compound, a layer bearing a tag, offering better mechanical strength, or simply staining the particles with a colour, etc.

For those applications in which the selective uptake of the core-shell particles in particular biological cells is desirable, the outer layer of the core-shell particles might be covalently bound to antibodies specific to the particular biological cells.

The particle for use as a host for the active substance in a sustained release formulation has to exhibit the following properties:

The pores should be interconnected in all three spatial directions in the same way, e.g. the material structure should belong to a cubic space group.

The material of the particle should offer a core-shell superstructure, whereas the shell should substantially hinder the diffusion of the active substances.

Diffusion of the active substances in the core should be as high as possible, optionally enabled by a liquid transport phase.

The particle distribution should be monodisperse, i.e., offer a standard deviation (SDV) in particle diameter generally of less than 15% of the mean particle size and in some aspects of the disclosure of less than 10% of the mean particle size.

The size of each individual particle should be greater than 1 µm, and in some aspects of the disclosure greater than 2.5 µm and in other aspects greater than 7 µm.

For large-scale applications, it should be possible to synthesize the material from readily available starting compounds of reasonable price, along simple synthetic routes.

The term "cubic crystal system" is to be understood as an isometric crystal system which shows reflections in X-Ray Pattern assignable to a cubic space group.

Crystal facets might be observed at the boundary surface of the particles. The term "facet" implies a flat surface having a geometric shape.

Figure 17:
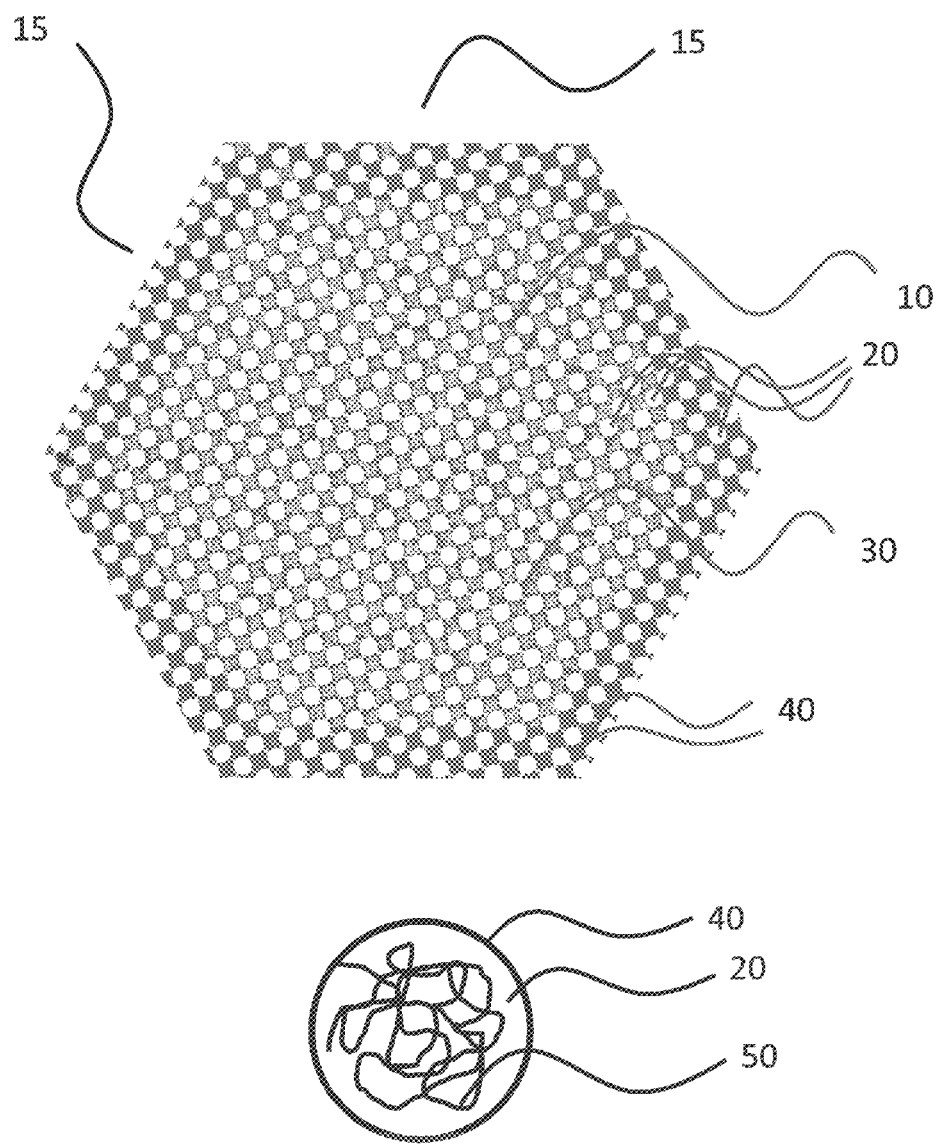
FIG. 17 shows an outline structure for the core-shell mesoporous particle of the disclosure.
Figure 22:
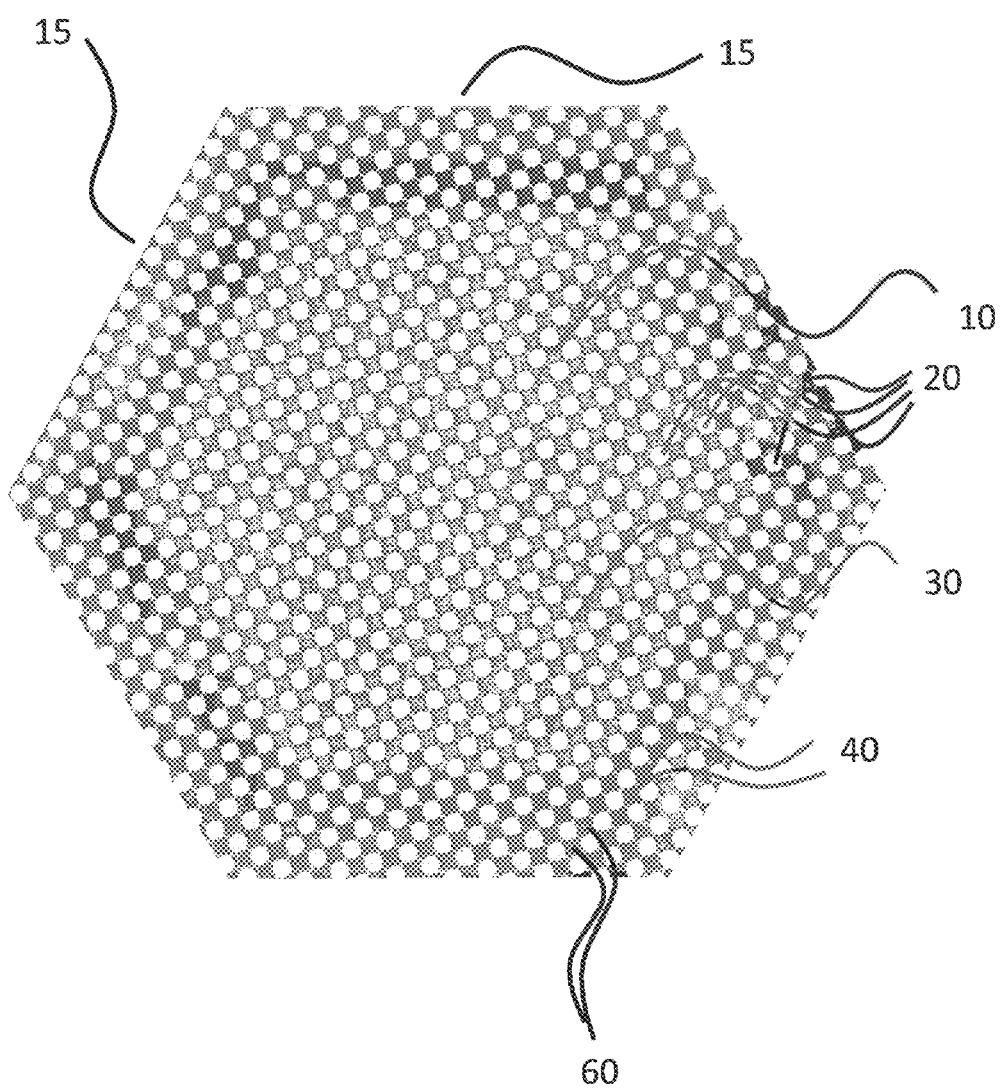
FIG. 22 shows an outline structure for a core-shell mesoporous particle with two shells.

FIG. 17 shows an example of a structure of a particle 10 that fulfills these requirements. The particle 10 comprises a plurality of interconnected pores 20 in both a core 30 and a shell 40 and show facets 15 The interconnected pores 20 in the shell 40 have restrictions 50 within the interconnected pores 20. The particle 10 can be filled with an active substance. The restrictions in the shell 40 restrict elution of the active substance from the particle 10. It will be appreciated that further ones of the shells 40 can be added. The interconnected pores have dimensions in the nanometer range. FIG. 22 shows an example of a structure of a particle 10 with an additional shell 60.

The properties of the core-shell particle material disclosed herein have been improved by the application of the disclosed synthetic procedures. In comparison with the methods known in the literature, for example "Control of Crystal Morphology of SBA-1 Mesoporous Silica", S. Che et al, Chem. Mater. 13 (2001) 2237, profound changes in the synthetic procedure and the compositions of the starting materials have been made.

It is known that the use of two different types of surfactant instead of a single surfactant in the synthesis of the porous particles can influence the phase dispersity, shape and mean size of the obtained porous particles. This is described in "*Morphology and porosity characteristics control of SBA-16 mesoporous silica. Effect of the triblock surfactant Pluronic F127 degradation during the synthesis*", M. Mesa et al., Solid State Science 7 (2005) 8, 990-997. The inventors have found that the simple use of two surfactants instead of a single surfactant, i. e. a combination of an ionic surfactant, such as a tetraalkylammonium salt, and a non-ionic surfactant such as, for example, Pluronic F127, PE105 or F108, is insufficient for obtaining the porous particles with the desired properties.

Addition of inorganic salts can also improve the properties of ordered mesoporous materials, as described in *"Non-ionic Block Copolymer Synthesis of Large-Pore Cubic Mesoporous Single Crystals by Use of Inorganic Salts"*, C. Yu, J. Am. Chem. Soc. vol. 124 (2002) 17, p. 4556. A simple combination of both techniques, e.g. using the co-surfactant and adding the inorganic salt does not lead to the desired material properties for the core-shell particles disclosed herein.

The inventors have surprisingly discovered that, in order to achieve the material homogeneity, e.g., desirable size distribution and monodispersity, a co-solvent with appropriate properties has to be introduced into the reaction mixture. Additionally, the mixing order has to be altered from the mixing order common in the art.

The inventors have established that the desirable material properties are achieved when the following conditions of the synthesis are fulfilled:

A mixture of a cosolvent with a non-ionic surfactant of the poloxamer type (sub group of polyalkylene oxide), such as Pluronic F127, and a silicon source, such as TEOS, is prepared shortly before its addition under vigorous stirring to a mixture of the suitable ionic surfactant and the inorganic salt, both of which are dissolved in diluted hydrochloric acid.

The co-solvent possesses a dielectric constant of more than 30, and its structure includes a negatively polarized oxygen atom.

Table 2 gives an overview of the obtained results in the view of the reagents mixing order, presence of a co-surfactant and various co-solvents.

TABLE 2

| 1 Example | 2 FIG. | 3 F127 | 4 Mixing order | 5 Cosolvent | 6 $\epsilon_{cosolvent}$ | 7 Structure | 8 $\mu \pm \sigma$ [μm] ($\sigma/\mu$*100%) | 9 Lewis basic group | 10 Comment |
|---|---|---|---|---|---|---|---|---|---|
| 1 | 1 | No | standard | — | — | — | — | — | strong aggregation |
| 2 | 2 | Yes | standard | — | — | — | — | — | strong aggregation |
| 3 | 3 | Yes | standard | DMF | 38 | (structure) | — | Yes [O] | strong aggregation |
| 4 | 4 | Yes | other | DMF | 38 | See example 3) | 1.6 ± 0.32 (20%) | Yes [O] | some aggregates |
| 5 | 5 | No | standard | DMF | 38 | See example 3) | — | Yes [O] | strong aggregation |
| 6 | 6 | No | adapted | DMF | 38 | See example 3) | — | Yes [O] | strong aggregation |
| 7a | 7a | No | adapted | DMC | 3 | (structure) | — | No | not cubic |
| 7b | 7b | Yes | adapted | acetic acid | 6 | (structure) | — | No | not cubic |
| 7c | 7c | Yes | adapted | THF | 8 | (structure) | 2.8 ± 0.92 (33%) | No | large SDV |
| 7d | 7d | Yes | adapted | 2-butanone | 19 | (structure) | 2.4 ± 0.94 (39%) | No | large SDV |
| 7e | 7e | Yes | adapted | acetone | 21 | (structure) | 2.6 ± 0.81 (31%) | No | large SDV |
| 7f | 7f | Yes | adapted | ethanol | 25 | (structure) | 2.0 ± 0.65 (33%) | No | large SDV |

TABLE 2-continued

| Example | FIG. | F127 | Mixing order | Cosolvent | $\varepsilon_{cosolvent}$ | Structure | $\mu \pm \sigma$ [µm] ($\sigma/\mu*100\%$) | Lewis basic group | Comment |
|---|---|---|---|---|---|---|---|---|---|
| 7g | 7g | Yes | adapted | NMP | 32 | N-methylpyrrolidone structure | 3.0 ± 0.33 (11%) | Yes [O] | acceptable |
| 7h | 7h | Yes | adapted | DMPU | 36 | DMPU structure | 3.1 ± 0.34 (11%) | Yes [O] | acceptable |
| 7i | 7i | Yes | adapted | acetonitrile | 37 | CH$_3$—C≡N | 2.8 ± 0.50 (18%) | Yes [N] | some aggregates |
| 7j | 7j | Yes | adapted | DMF | 38 | DMF structure | 2.2 ± 0.26 (12%) | Yes [O] | acceptable |
| 7k | 7k | Yes | adapted | DMA | 39 | DMA structure | 3.3 ± 0.30 (9%) | Yes [O] | acceptable |
| 7l | 7l | Yes | adapted | DMSO | 47 | H$_3$C—S(=O)—CH$_3$ | 2.6 ± 0.34 (13%) | Yes [O] | acceptable |
| 7m | 7m | Yes | adapted | formamide | 111 | H—C(=O)—NH$_2$ | 2.0 ± 0.22 (11%) | Yes [O] | acceptable |

A complete mechanistic explanation for the experimentally found results has not been developed. The role of the non-ionic co-surfactant in the solution and its interactions with the additional solvent remain unclear. The necessity to mix the non-ionic co-surfactant with the co-solvent and the silicon source prior to adding the mixture of the non-ionic co-surfactant with the co-solvent to the rest of the reaction mixture cannot be explained on the base of current theory.

The dielectric constant of the additional solvent reflects the miscibility of the solvent with the silicon source, non-ionic co-surfactant and water to a certain extent. However, it is not the only precondition for a successful synthesis procedure, since solvents with a Lewis-basic nitrogen atom instead of an oxygen atom, even having a similar dielectric constant do not lead to good results (e.g. acetonitrile).

With the above-described variations of the reaction conditions, it was possible to obtain regularly faceted particles with narrow size distributions and an interconnected pore system. The particles exhibited a cubic crystal structure, as determined by X-ray Diffraction (XRD). The crystal morphology is described by a a octadecahedron (6 squares and 12 hexagonal planes) to which four three-fold rotation axes can be clearly assigned and hence is considered to be the cubic system. The particular crystal morphology observed within this disclosure is described more in detail in "Synthesis of MO-SBA-1 catalyst via sol-gel process and its activity", S. Wongkasemjit et al, Materials Chemistry and Physics, vol. 117, (2009) 1, p. 301. "By comparison with XRD-Pattern disclosed in Literature, it was found that particles belong to the cubic structure named SBA-1, comprising a highly interconnected channel system. This versatile process allows for the design of complex types of the core-shell particles having multiple shells, while still preserving the monodisperse size distribution without formation of aggregates. This approach enables a zero-order release kinetic in our release system.

The variations of synthesis parameters were investigated in order to allow an epitaxial growth of optionally organically modified silica precursors avoiding secondary nucleation, and thus creating the monodisperse core-shell particles with a substantially consistent shell thickness for all the core-shell particles in a batch. Hydrolysis rate, nucleation rate, precursor concentration, available specific surface area for epitaxial growth, or precursor amount for controllable shell thickness are only some factors that had to be considered during the synthesis.

The standard host material for the disclosed sustained release formulations comprises the particle 10 with the core 30 made of pure $SiO_2$; a first shell 40 comprises free —SH groups to which, via further modifications, organic molecules or polymers are bound covalently as the restrictions 50, and a second shell with the same composition as the core 30. The second shell was mainly introduced to better visualize the —SH group-containing shell via SEM techniques, as described in the experimental section, but might also serve for further chemical modifications, especially if bearing reactive chemical groups, like —$N_3$ or —Cl. Exemplary synthesis of such particles is described in the experimental section Extensive work showed that dextran with a molecular weight of ca 10000 is suitable to act as a restricting agent that decreases the diffusivity of the incorporated active substance in the first shell of the host material. The release kinetics exhibited the theoretical predicted zero-order behavior. The use of dextran derivatives, as demonstrated in Tables 3 and 4, was surprisingly advantageous than the use of known pore blockers, such as cyclodextrins.

Tables 3 illustrate the time by which half of the active substance (9-aminoacridine and labeled gentamicin) is released from the depot formed by the assembly (see also description in Examples "Recording Release Curves"). Abbreviation 9-AA in the table stands for 9-Aminoacridin. For a better description of this substance and also labeled gentamicin reference is made to the experimental section of this disclosure. The half time for the release of labeled gentamicin was extrapolated from the known reservoir size and the total released substance after 60 days.

TABLE 3

| Product | $t^{1/2}$ |
|---|---|
| No capping, released substance: 9-AA | 6 min |
| Hydroxypropyl-β-cyclodextrin, released substance: 9-AA | 25 min |
| Dextran-10 (capping via click cycloaddition reaction), released substance 9-AA | ca. 5000 min |
| Dextran-10 (capping via Michael maleimide reaction), released substance: labelled gentamicin | ca. 60 days |

It can be seen from Table 3 that a so-called "capping" method can be used to decrease diffusivity of the active substance in the shell 40 of the particle 10. This capping method involves the introduction of organic molecules as the restrictions 50 into the particle 10, optionally in a polymeric form, that decrease the effective pore diameter of the interconnected pores 30 of the shell 40 of the particle 10 by more than 10%, and is performed by covalent bonding of an organic moiety of the capping reagent to the chemically modified pore walls in the shell. The covalent bond is optionally formed by using a cycloaddition reaction between an alkyne and an azide ("click reaction"), or by other conjugation methods known in the art, such as but not limited to a reaction between a thiol and maleinimides, between acid activated esters and amines etc.

As model compounds for the release kinetics study, 9-aminoacridine (9-AA) and a conjugate between 9-AA and gentamicin were used. 9-Aminoacridine is a low-toxic antiseptic and gentamicin is a aminoglycoside antibiotic. It and its conjugates can be easily detected and quantitated in aqueous solutions due to strong fluorescence by means of a fluorimeter.

Applications

The particles of the disclosure have a number of potential applications. Examples are:

Releasing steroid hormones such as testosteron from a parenteral polymer extrudate with incorporated hormone-containing particles in case of low testosterone levels in the body.

Releasing thyroid hormones from a partenteral polymer extrudate with incorporated hormone particles in case of hypothyroidism.

Releasing biocides such as zinc pyrithione by incorporated biocide containing particles in shoes or socks to reduce unpleasant smell formation.

Releasing biocides such as zinc pyrithione by incorporated biocide containing particles in tubes or hoses to prevent fouling.

Releasing biocides such as zinc pyrithione by incorporated biocide containing particles in lacquers to prevent fouling.

Releasing pesticides such as allethrin or permethrin on fields;

Releasing antibiotics such as gentamicin in glues to prevent biofilm formation.

Release of anti tumor drugs during chemotherapy.

The particles of the disclosure can incorporate a variety of different active substances. Non-limiting examples are summarized below.

Steroid hormones: medroxyprogesterone acetate, progesterone, estradiol, norgestrel;
Peptide hormones and their analogs: leuprolide acetate, octreotide acetate, triiodothyronine;
Antipsychotics: risperidone, flupentixol, olanzapine;
Antibiotics: gentamicin, vancomycin, tobramycin;
Antineoplastics: paclitaxel, etoposide, topotecan, cytarabine;
Immunosuppressors: rapamycin;
Non-steroid anti-inflammatory: diclofenac, nabumethone;
Analgetics: hydromorphone, buprenorphine;
Antidiabetics: pioglitazone, gliclazide.
Anti-tumor drugs: Cisplatin, Carboplatin

EXAMPLES

The next section describes experimental protocols for synthesis of the material that fulfils the requirements for a zero-order release kinetics.

This section is divided in 6 Parts, namely
Reagents, Synthesis of raw materials
Analysing Techniques
Synthesis of Host Materials
Loading of Host Materials with AS
Capping
Release Experiments Reagents, Synthesis of Raw Materials Unless otherwise noted, all chemicals were purchased from Sigma-Aldrich in reagent grades. Reactions were performed at room temperature. Water was deionised.

Cetyltriethylammonium Bromide:

Into a 2 L round-bottom flask was placed hexadecyl bromide (250 g), 2-methoxypropanol (250 mL), and triethylamine (200 mL). The flask was heated without stirring at 75° C. for 96 h and the contents were concentrated on a Rotavap at 75° C. and 20 mbar. To the residue, methyl tert-butyl ether (800 mL) was added. The slurry was vigorously stirred by a mechanical stirrer for 12 h, filtered, washed with 3 portions (400 mL each) of methyl tert-butyl ether, and dried in vacuum to obtain the product as a white solid in nearly quantitative yield.

9-Aminoacridine (Base):

9-Aminoacridine hydrochloride monohydrate (2.5 g) was mixed with 5% aq. $NH_3$ (25 mL), stirred for 3 h, filtered, washed with water (30 mL), THF (30 mL), and dried in vacuum.

4-Azidobutyryldextran-10 Solution:

In a 100 ml round-bottom flask under argon, 1,1'-carbonyldiimidazol (3.0 g) was dissolved in dry DMSO (25 mL), and 4-azidobutyric acid (1.5 g) was added. After 3 h, dry dextran-10 (4.5 g) was added, and the mixture was heated under argon at 75° C. for 18 h. On cooling, ethanol (300 mL) was added to the mixture. The oily precipitate was washed 4 times with boiling ethanol (100 mL portions), and dried at 60° C. The residual solid was dissolved in water to obtain a 10% solution that was filtered using 0.22 µm syringe filter and used without further purification. 4-Azidobutyryl-hydroxypropyl-β-cyclodextrin: In a 250 mL round-bottom flask, dicyclohexylcarbodiimide (6.0 g) was dissolved in dry DMF (30 mL), and 4-dimethylaminopyridine (3.4 g) was added. To this solution, hydroxypropyl-β-cyclodextrine (8.0 g, Aldrich, average Mw=1460 Da) was added, and the mixture was stirred for 5 days at ambient temperature. Solvent was removed in vacuum, the residue separated between $CH_2Cl_2$ (50 mL) and deionized water (100 mL), aqueous layer extracted twice with $CH_2Cl_2$ (50 mL), and passed through a column containing ion-exchange resins: 35 g of Amberlyst 15 in $H^+$-form and 35 g of Amberlyst A26 in $OH^-$ form. The column was washed with 100 mL of deionized water, the solutions were combined, concentrated in vacuum to ca. 25 mL, and lyophilized. The product was obtained as colourless foam.

4-Maleimidobutyryldextran-10:

4-Maleimidobutyryldextran-10 was obtained from 4-maleimidobutyric acid (as described in R. M. de Figueredo, P. Oczipka, R. Fröhlich, M. Christmann, *Synthesis*, 2008, (8), 1316-1318) and Dextran-10 as described in: K. Peng, I. Tomatsu, A. V. Korobko, A. Kros *Soft Matter*, 2010, (6), 85-87.

Aminoacridin-Labelled Gentamicin:

9-Isothiocyanatoacridin (100 mg) was dissolved in MeOH (5 mL), and added to the solution of gentamicin sulfate (250 mg) in 5 mL MeOH and some drops of water, followed by the solution of BaO (100 mg) in 5 mL MeOH. The suspension was stirred 30 min, neutralized with 3% H2SO4 in MeOH, filtered, evaporated to dryness and the residue was washed carefully with dichloromethane. Obtained 297 mg of yellow powder.

3-Azidopropyltriethoxysilane

To a solution of 3-chloropropyltriethoxysilane (2.31 g, 9.6 mmol) and tetrabutylamonium iodide (0.020 g, 0.05 mmol) in butanone (25 mL) was added sodium azide (3.120 g, 48 mmol) and the reaction mixture was heated under reflux for 50 h. Filtration over celite was followed by evaporation of the solvent under vacuum. The residue was dissolved in dichloromethane (150 mL) and then washed with water (2 times 20 mL). The organic phase was dried (NaSO4) and evaporated to give the desired product (1.9 g).

Analysing Techniques

Sorption isotherms were recorded with a Quantachrome NOVAe using nitrogen at 77 K. Samples were degassed for 12 h in vacuum at 393 K prior to measurement. Surface area was determined via the BET-Algorithm, pore size distribution via BJH-Algorithm applied to the desorption branch.

Powder-X-ray diffraction was recorded on a Bruker D8 using Cu-kα radiation and 0.07° 2-theta steps.

Scanning electron micrographs were recorded with a Phenom G1 from Phenom-World BV.

Particle size distribution was determined from SEM Images using the software ImageJ.

Light microscopic Images were carried out using a Nikon TiE Fluorescent microscope.

The core-shell superstructures were made visible in SEM-Micrographs by partly breaking the particles and improving the contrast between the cores and the shells by increase of the electron density through the binding of gold(III) ions to SH-groups in the shell(s). Samples were partly destroyed by gentle grinding. Approximately 20 mg of the gently ground powder was stirred for 20 minutes in 5 ml of 1.5 mM aqueous $AuCl_3$, and washed thoroughly with water and acetone on a Buchner funnel After drying on the Buchner funnel, SEM pictures were immediately recorded as soon as the sample exhibited a slightly yellow colour.

The concentrations of the released substances were determined by calibration curves after measuring the fluorescence of diluted aliquots using a Hoefer DynaQuant 200 Fluorometer.

Synthesis of Host Materials

For all experiments, a Stock Solution S1 was prepared by dissolving 11.54 g of cetyltriethylammonium bromide and 141 g of sodium sulphate in 1190 mL of 3.36 M aqueous hydrochloric acid. The solution was stored overnight at ambient conditions prior to its first use. Stock Solution S2 was prepared by dissolving 10 g of Pluronic F127 in 100 g of N,N-dimethylformamide.

Examples Evaluating the Influence of Cosolvents, Pluronic F127 Template and Mixing Order.

All experiments were carried out by mixing 20 g of Solution S1 with optional additives. This solution was named A1. To the prepared A1 solution, a mixture named A2, comprising 0.3 g TEOS and optional additives was added, stirred for 20 seconds, and stored for 30 minutes on the bench. The mixture was transferred to a rotary shaker and stirred with 1 RPM for 90 minutes, filtered, the solid washed with water and dried. Table 4 displays the compositions of A1 and A2. The number of examples refers to numbers in the first column in Table 2

TABLE 4

| Example | A1 | A2 |
|---|---|---|
| 1 | 20 g S1 | 0.3 g TEOS |
| 2 | 20 g S1, 0.1 g F127 | 0.3 g TEOS |
| 3 | 20 g S1, 0.1 g F127, 1 g DMF | 0.3 g TEOS |
| 4 | 20 g S1, 0.1 g F127 | 1 g DMF, 0.3 g TEOS |
| 5 | 20 g S1, 1 g DMF | 0.3 g TEOS |
| 6 | 20 g S1 | 1 g DMF, 0.3 g TEOS |
| 7a-m | 20 g S1 | 1 g cosolvent, 0.1 g F127, 0.3 g TEOS |

Examples 7a-7m were carried out similarly, however, the co-solvent used was the solvent listed in Table 2.

The reaction mixture in example 7j was heated in an autoclave for 2 hours at 120° C., the white suspension was filtered off by a Buchner funnel, and placed in a bottle with 200 ml of the mixture of 10% wt. conc. HCl and 90% wt. of ethanol. This treatment was repeated twice, then the solid was washed with isopropanol and dried at 90° C.

Figure 8:
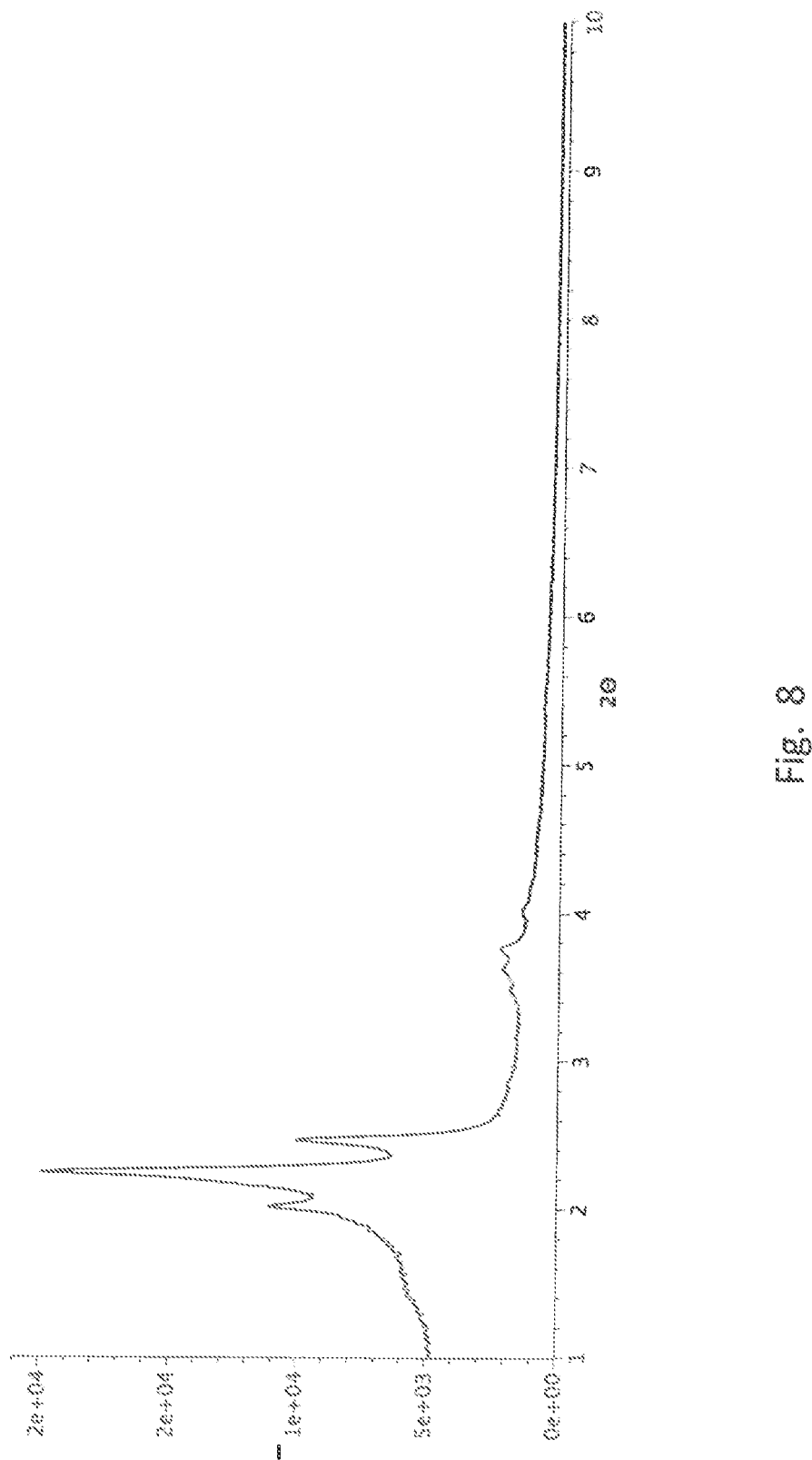
FIG. 8, 9, 10 depict XRD pattern, sorption isotherm and BJH pore size distribution of Example 7j of Table 2.
Figure 9:
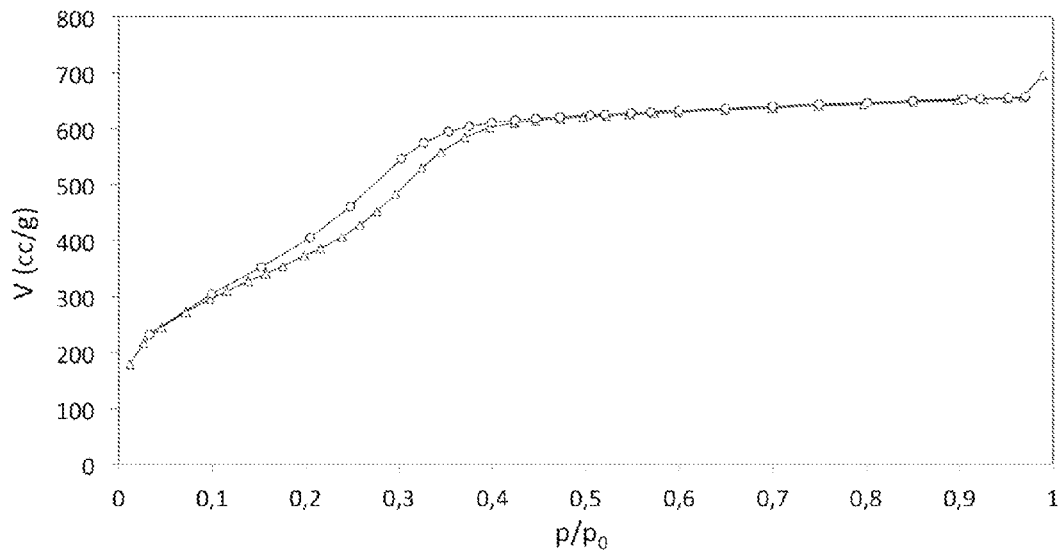
Figure 10:
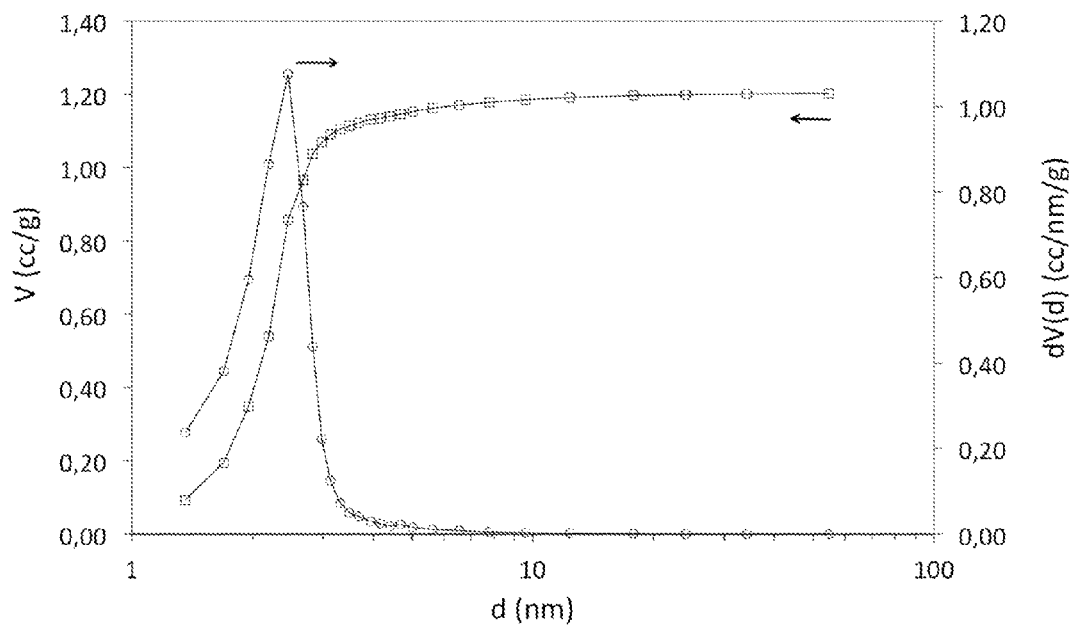

The XRD pattern of this material is displayed in FIG. 8, the sorption isotherm in FIG. 9 and pore size distribution in FIG. 10. The XRD reflections were assigned to a cubic structure, with reflections [200] at 2.02°2θ, [210] at 2.25°2θ and [211] at 2.465°2θ.

In all other experiments the phase purity was checked via XRD measurements without template extraction.

Standard Host Material Used for Release Experiments.
Synthesis of the Core 3.3 g of Solution S2 was mixed with 0.9 g of tetraethoxysilane, the obtained clear solution was poured into 60 g of Solution S1, stirred vigorously for 20 seconds. This mixture was named "Reactant Solution 1" (R1). The solution was stored at ambient conditions of 30 minutes and then put into a rotary shaker (1 RPM) for another 30 minutes in a plastic vessel, offering a total volume of ca. 75 ml.

The second Reactant Solution (R2) was prepared 1 hour after having started with R1, in the same manner. However, all the reagents quantities were multiplied by a factor of 5. Additionally, after mixing S1, TEOS and S2, the previously prepared solution R1 was added, and 340 g of the final mixture were immediately placed in a rotary shaker for 2 hours and 15 minutes at 1 RPM. The vessel used had a total volume of ca. 350 ml.

Synthesis of First Shell Containing SH Functional Groups

A reactant solution R3 similar to R1 and R2 was prepared 2 hours and 15 minutes after having started preparing solution R2. The reagents quantities were multiplied by a factor of 5.7 of the ones used to prepare R1, and TEOS was replaced by a mixture of 95% wt. of TEOS and 5% wt. of 3-mercaptopropyltriethoxysilane. This solution was added to 340 g of the mixture consisting of R1 and R2, and placed in a rotary shaker for 3 hours at 1 RPM, in a vessel with the volume of ca. 102% of the total volume of the liquids. The 3-mercaptopropyltriethoxysilane is responsible in this example for the creation of the —SH functional groups.

Synthesis of a Second Shell with Pure TEOS as a Silicon Source

A reactant solution R4, similar to R1, was prepared 3 hours after having started the preparation of R3. The reagents quantities were multiplied by a factor of 8.3. The previously prepared mixture containing solutions R1, R2 and R3 (ca. 700 g) were added to R4. The resulting suspension was kept in a rotary shaker for 2 hours at 1 RPM in a vessel of the volume of ca. 102% of the total volume of the liquids. Two hours after having started preparing Solution R4, the suspension was filtered, the white solid was washed from the filter into a glass bottle using ca. 200 ml of diluted (3%) hydrochloric acid with same concentration of Templats Pluronic F127, cetyltriethylammonium bromide and Sodiumsulfate, as in Reactant solution R1, and the closed bottle was placed in an oven at 90° C. overnight.

Template Removal

The white suspension was filtered off on a Buchner funnel and placed in a bottle with 200 ml of a mixture of 10% wt. conc. HCl and 90% wt. of ethanol for several hours in a shaker. This treatment was repeated twice, then the solids were washed with isopropanol and dried at 90° C.

Figure 11:
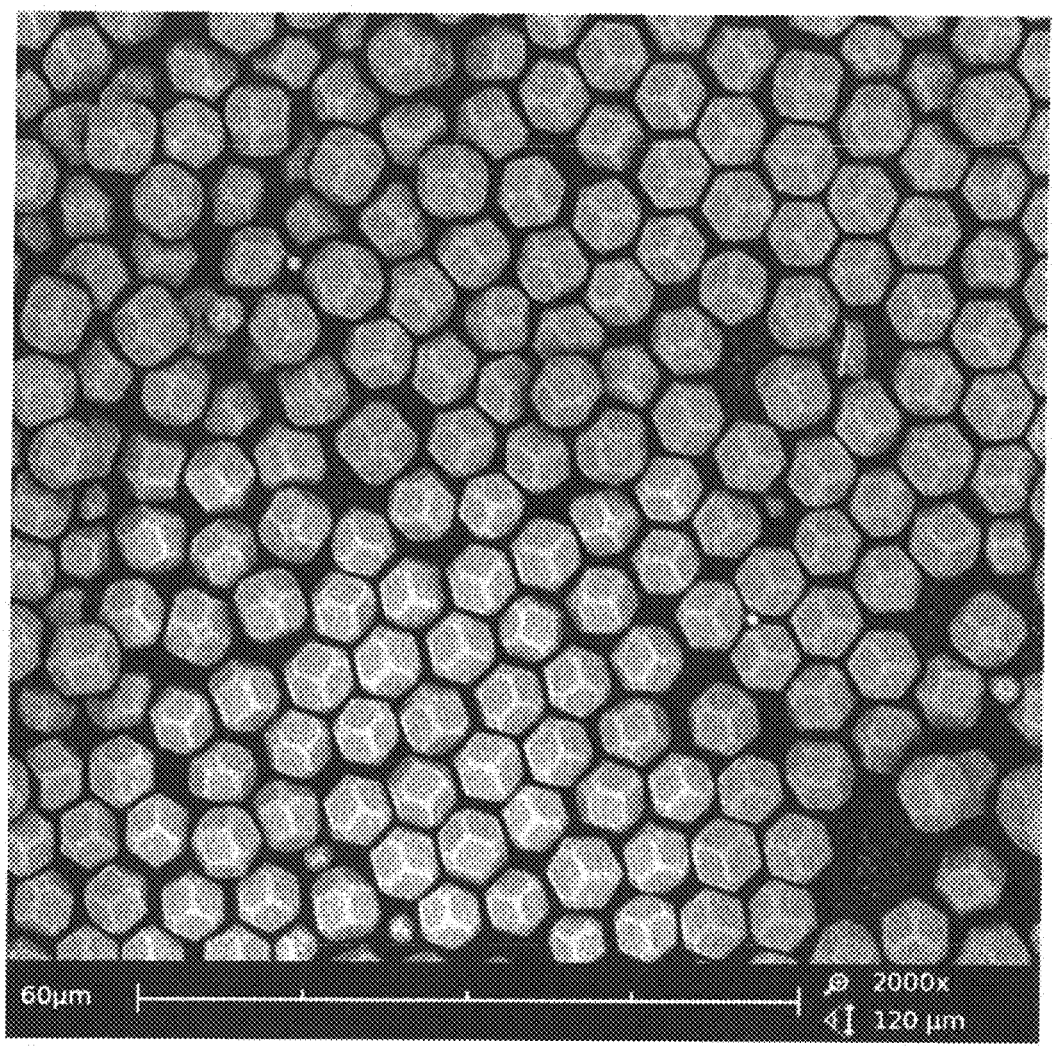
FIG. 11 shows a representative example of standard host material for encapsulation experiments NCap-1.
Figure 12:
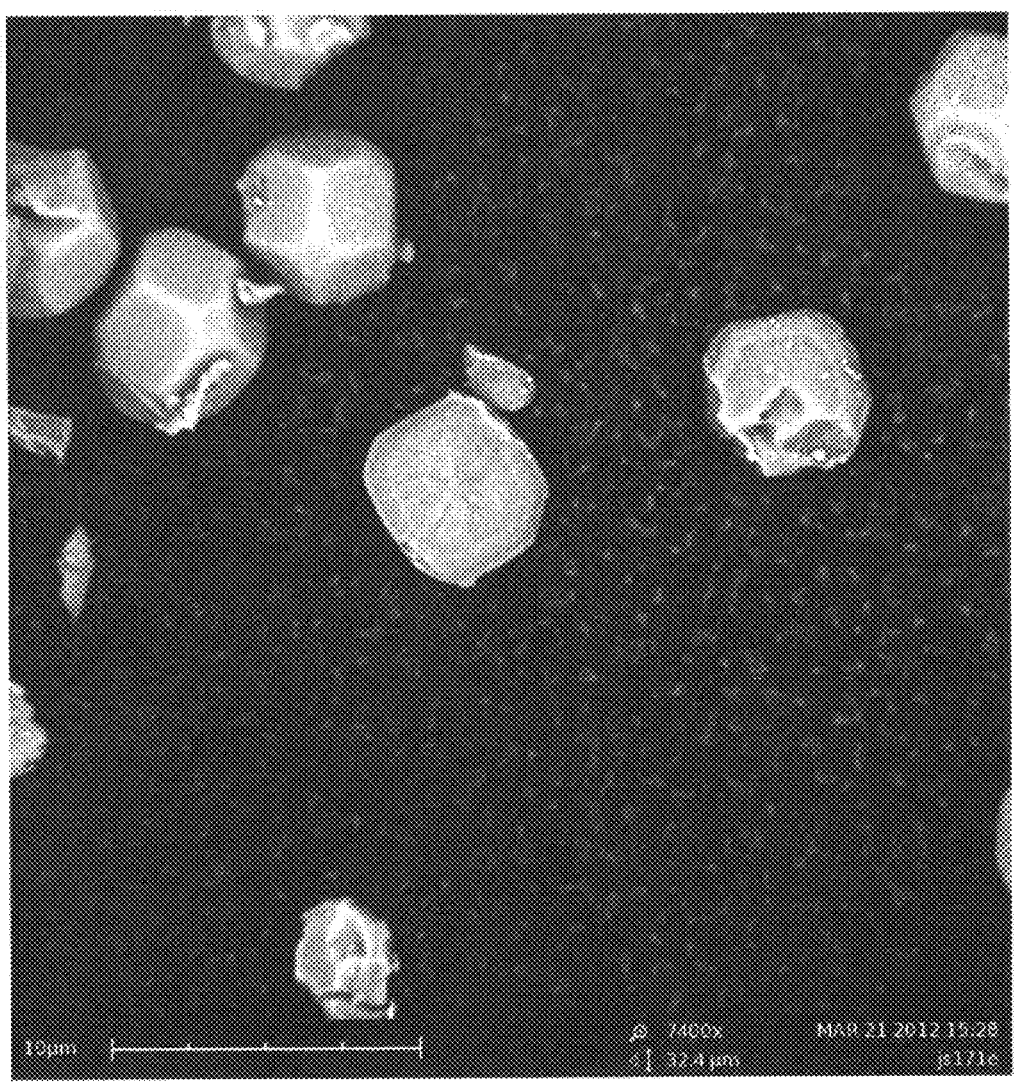
FIG. 12 and FIG. 13 show SEM pictures of the achieved Core-Shell Superstructure.
Figure 13:
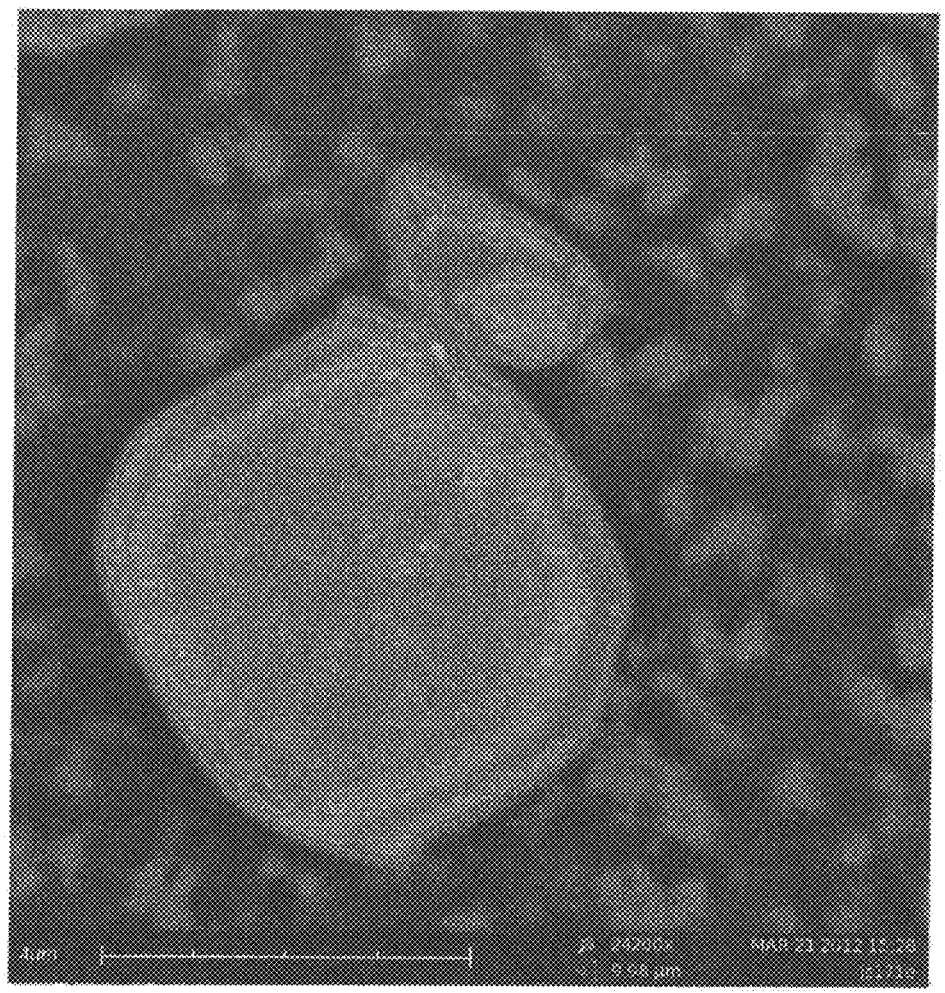

The sample so obtained consisted of pure SBA-1 mesoporous silica with a cubic structure, as was determined by XRD, and exhibited a surface area of 1223 m$^2$/g with the pore size diameter of 2.2 nm. The mean diameter of particles was 6.76±0.61 μm (9%). A SEM-Picture is displayed in FIG. 11 in which the cubic crystal morphology of decaoctahedrons is clearly visibly. ASEM Picture of shells is depicted in FIG. 12 and FIG. 13. This material was named NCap-1.

Propargylation of —SH Groups 3.3 g of NCap-1, bearing free SH-groups in one of the shells, was added to a mixture of 2-methoxypropanol (15 mL), diisopropylethylamine (1.2 mL), and propargyl bromide (1 mL of 80% toluene solution). This suspension was allowed to react in a shaker for 24 h, filtered, washed with methanol and dried in vacuum.

Variation of Standard Host Material Altering the Chemical Composition of Core and Shell(s)

To support the versatility of the disclosed synthesis approach, the synthesis procedure was altered by using different silicon sources, e.g. not only 3-Mercaptopropyltriethoxysilane was used as 5% Additive to TEOS, as described under "Synthesis of first shell containing SH functional groups", but instead 3-Chloropropyltriethoxysilane, 3-Azidopropyltriethoxysilane and 3-Mercaptopropyltriethoxysilane were used as a 5% additive during synthesis of the core, the first shell and/or the second shell. Obtained products all showed the same appearance in SEM-Pictures, exhibited same SBA-1 structure as determined by XRD and had high specific surface areas of more than 1100 m$^2$/g as determined by sorption measurements. Table 5 gives an overview of investigated variations. Note: —Cl/—N$_3$/—SH means use of 5% 3-X propyltriethoxysilane, where X means —Cl/—N$_3$/—SH respectively.

TABLE 5

| Core | —SH | —SH | Pure TEOS | Pure TEOS | —SH |
|---|---|---|---|---|---|
| Shell 1 | Pure TEOS | —N$_3$ | —Cl | —N$_3$ | —N$_3$ |
| Shell 2 | Pure TEOS | Pure TEOS | —N$_3$ | —Cl | —Cl |

Figure 18:
FIG. 18 shows an optical image of fluorescent particles.

The sample with a core bearing —SH moieties and only one pure SiO$_2$ shell (e.g. second column in Tab. 5) was used for a fluorescent labelling experiment to support the core-shell structure by a second analysis method despite SEM Microscopy and to prove the penetration and localization of dextran inside the pore system of the material. FITC-dextran (Mw=3000-5000, Sigma) was converted into the 4-maleimidobutyryl adduct with same synthesis procedure as Dextran-10 as cited above. The labelled, e.g. fluorescent 4-maleimidobutyryl dextran (10 mg), was dissolved in 0.2 mL DI-H2O and mixed with 100 mg of the particles, containing SH-groups in the inner core. After 6 hours, the suspension was diluted with 10 mL H2O, sonicated for 3 min in an ultrasound bath, and the particles were separated by centrifugation. The washing/centrifugation process was repeated 4 times, and finally the solid was dried in vacuum. The obtained powder was resuspended in water and observed in a fluorescent microscope. FIG. 18 shows an image. The core is brightly illuminated, whereas the shell is much darker. The facets are visible.

Variation of Shell Thickness

Figure 19:
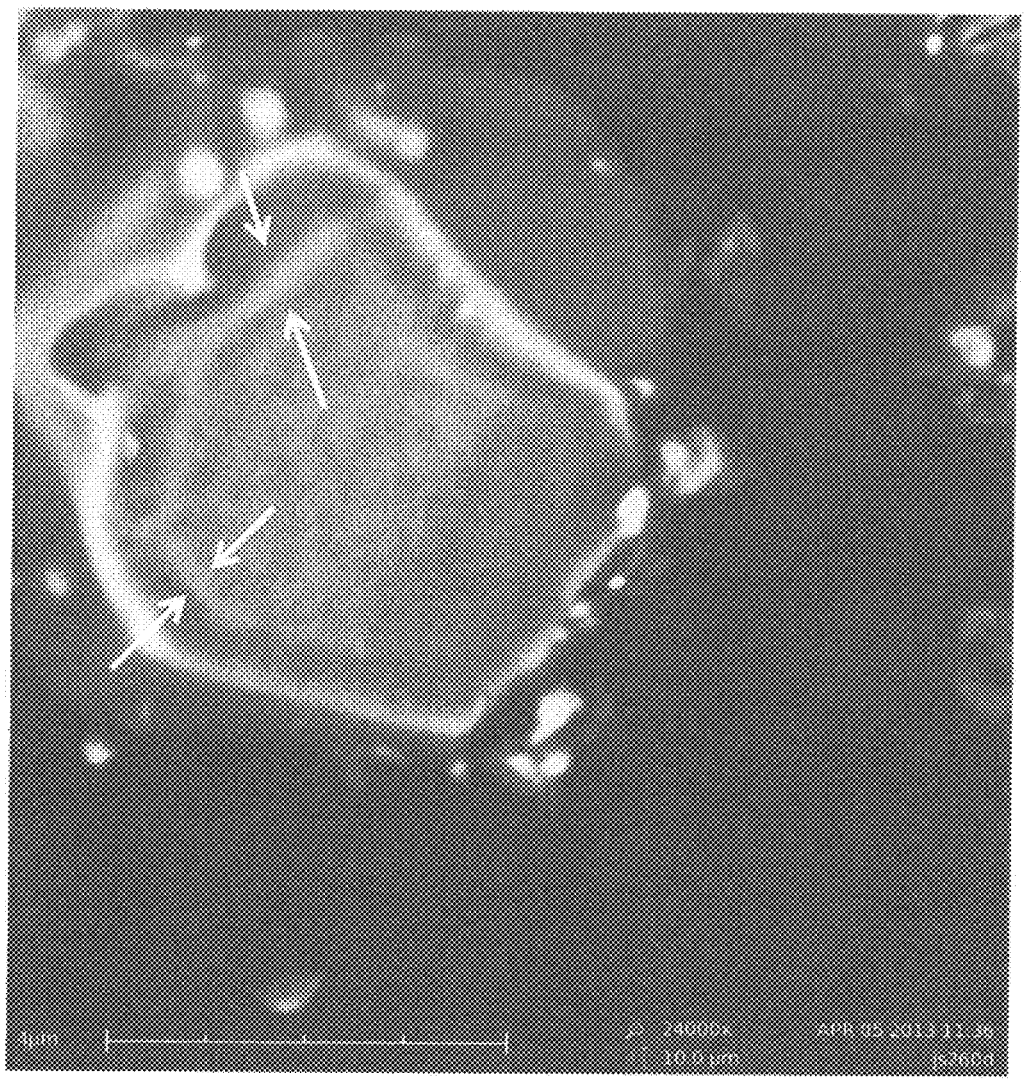
FIG. 19 shows a SEM Image of a partly broken particle with a thin shell of —SH containing groups made visible by gold incorporation.

The standard procedure was altered by simply varying the amount of R3, e.g the amount of R3 was divided by a factor of four. SEM Pictures revealed a much smaller SH-Containing Shell (see analysing Techniques for a detailed description of this technique). (See FIG. 19, thin shell is marked by arrows.).

Loading of Host Material with Active Substance 0.5 g of a 15% solution of 9-aminoacridine hydrochloride hydrate, or labelled gentamicin in DMF was dropped on 1 g of the NCap-1 (—SCH$_2$C≡CH, in case of the "click"-reaction, and —SH, if the Michael addition was supposed be used for capping). The powder was shaken in a 10 ml round bottom flask for 3 minutes and checked afterwards, whether any clustering took place. If so, the clusters were carefully ground with a spatula, and the powder was shaken for further 3 minutes. This process was repeated, until no more clustering was observed. The powder was dried in an oven at 80° C. for 2 days in an open vessel.

Capping

Capping with Dextran-10: "Click Reaction"

Figure 15:
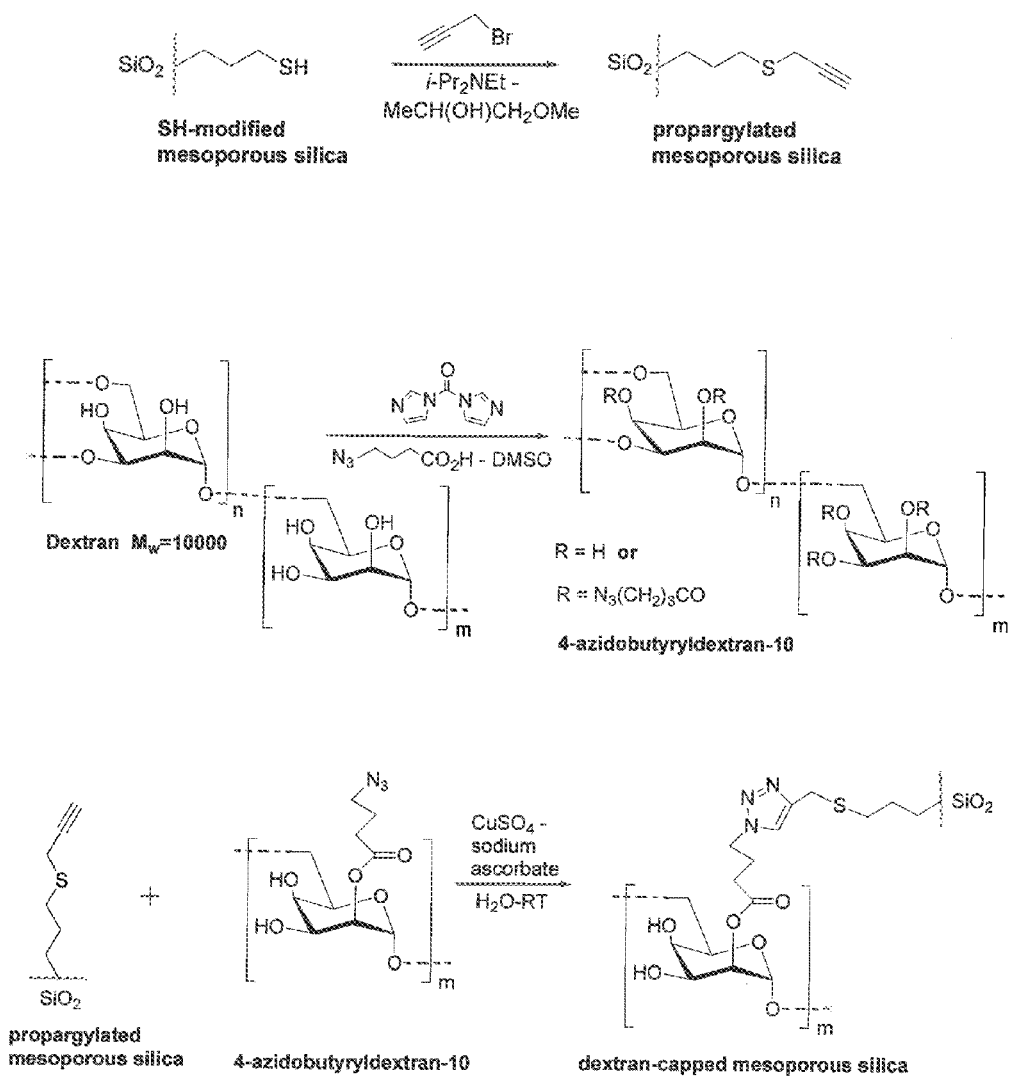
FIG. 15 shows reaction schemes for the capping procedure with dextrane.
Figure 16:
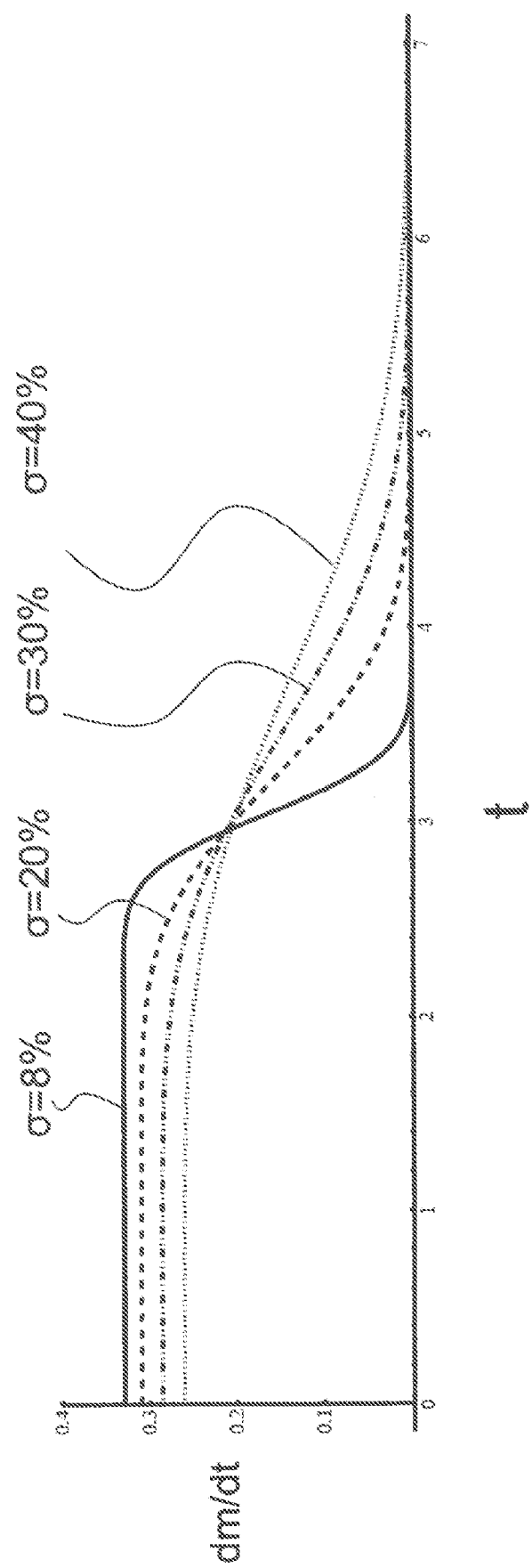
FIG. 16 depicts several theoretical release rate of particle assemblages with different SDV calculated from Eq. 7. Mean diameter $\mu$ was set to 3 a.u.

Propargylated, 9-aminoacridine-loaded NCap-1 (1.0 g) was mixed with 10% aq. solution of 4-azidobutyryldextran-10 (2 mL), and the sodium ascorbate solution, prepared from L-ascorbic acid (400 mg), and NaHCO$_3$ (200 mg) in water (2 mL). A 7% aq. solution of CuSO$_4$ (0.3 mL) was added, and the resulted suspension was placed in a shaker for 72 h at ambient temperature. The sodium ascorbate solution is used to reduce the CuSO$_4$ to Cu$^+$ ions which catalyse a cycloaddition reaction. Water (10 mL) was added, and the suspension was centrifuged. Washing with 5 mL portions of water and centrifugation was repeated until the amount of the substance in the wash water became negligible. The yellow solid was dried in vacuum. Final loadings in the range of 1.5-2 mass % was obtained. A scheme for the synthesis pathway is depicted in FIG. 15.

Capping with Hydroxypropyl-β-Cyclodextrin

The capping was performed according to the procedure for the capping with dextran "click reaction", but 10% solution of 4-azidobutyryl-hydroxypropyl-β-cyclodextrin was used instead of the corresponding dextran derivative.

Figure 21:
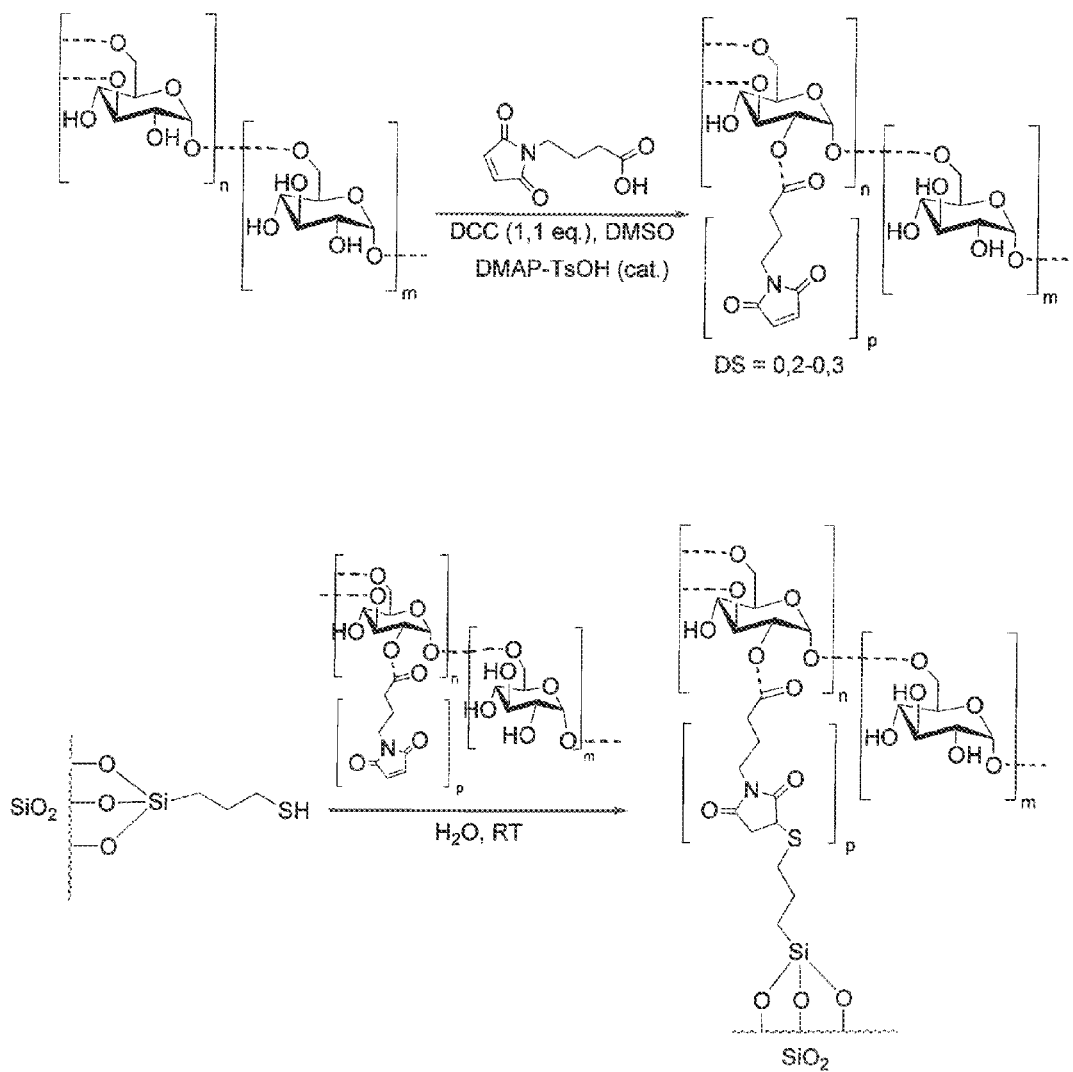
FIG. 21 shows a scheme for the "Michael addition" synthetic pathway.

Capping with Dextran-10: "Michael Addition":

Gentamicin-loaded NCap-1 (1.0 g) was mixed with 15% aq. solution of 4-maleimidobutyryldextran-10 (1 mL), and the resultant suspension was placed in a shaker for 24 h at ambient temperature. Water (10 mL) was added, and the suspension was centrifuged. Washing with 10 mL portions of water and centrifugation was repeated until the amount of substance in the wash water became negligible. The obtained yellow solid was dried in vacuum. A scheme for the synthesis pathway is depicted in FIG. 21.

Recording Release Curves 50 mg of the products obtained as described above (dextran-capped, hydroxypropyl-β-cyclodextrin-capped, or uncapped NCap-1, loaded with 9-aminoacridine hydrochloride) was washed thoroughly, placed into ca. 5 cm piece of a dialysis membrane (MWCO 10000-14000). The dialysis membrane was sealed and immersed into 200 mL of deionized water in a plastic beaker. The plastic beaker was fixed in a shaker. The water was changed each 24-48 h. For concentration measurements, s. fluorescence of the solution samples was measured (excitation 365 nm, emission 460 nm). The concentrations of the released compounds (9-aminoacridine or 9-AA-gentamicine) were determined using a calibration curve. The time by which a half of the substance was released from the sample was calculated. The results are given in Tables 3.

Figure 14:
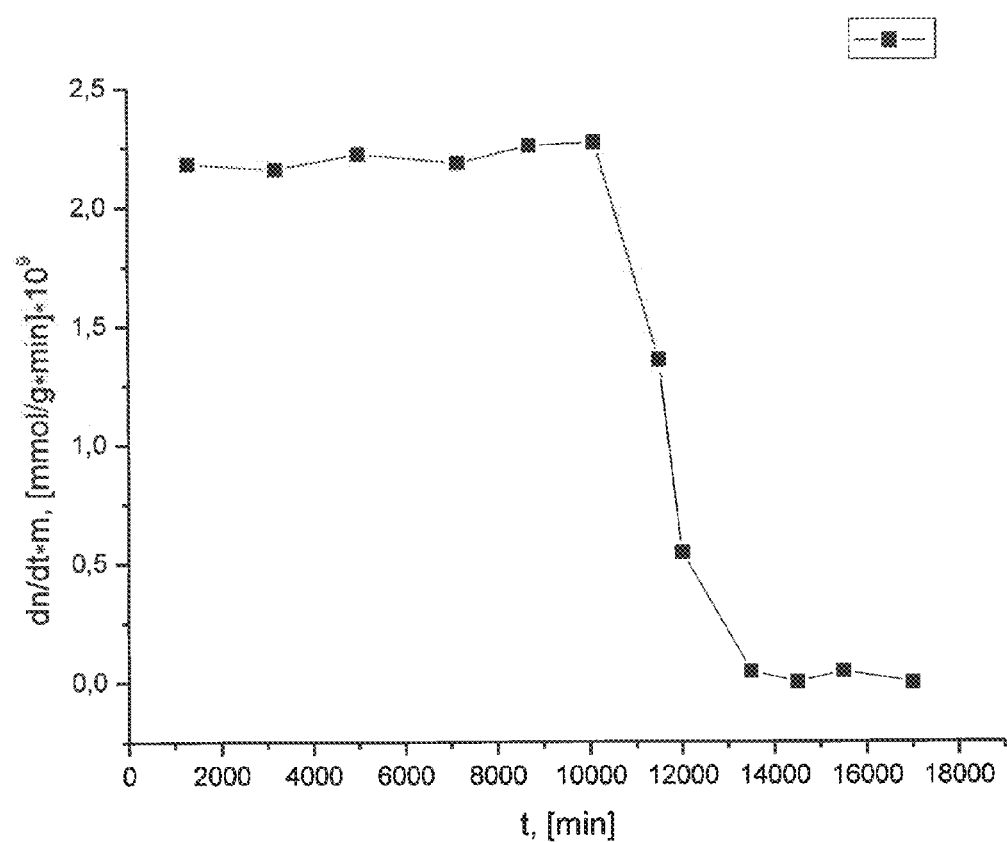
FIG. 14 shows the release rate versus time of encapsulated 9-aminoacridine.
Figure 20:
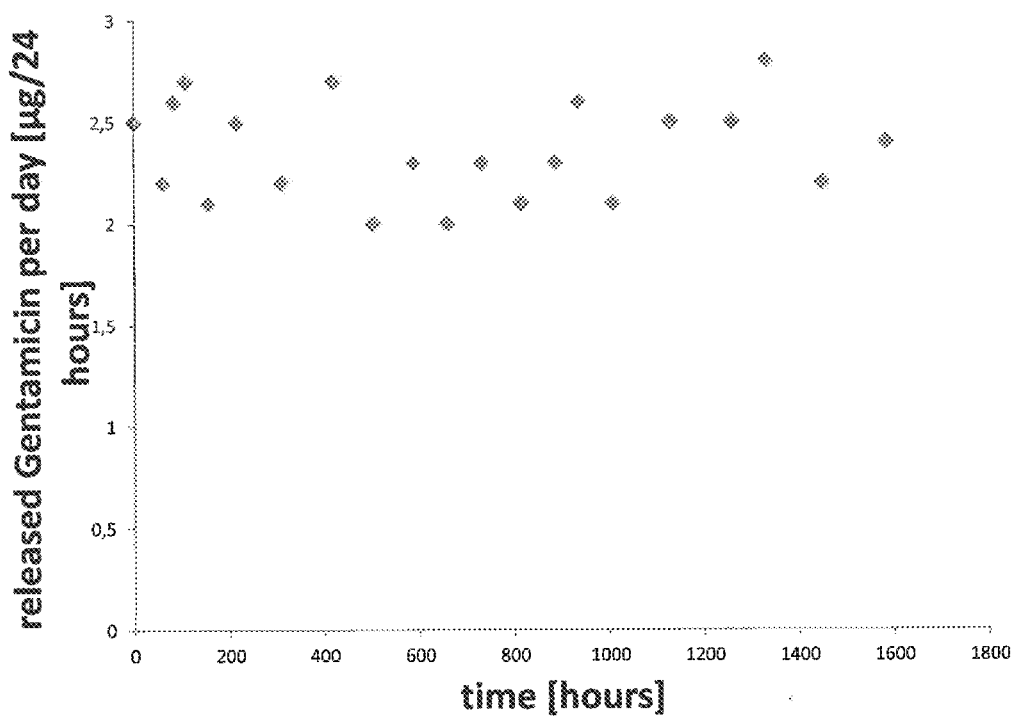
FIG. 20 shows the release curve of labelled antibiotic Gentamicin over 65 days.

From the obtained concentrations the release of the active substance per time was calculated. The dependency of the release rate on time for the dextran-capped NCap-1 is depicted in FIGS. 14 and 20

The invention claimed is:

1. An assemblage of particles having interconnected nanosized core pores in a nanoporous core with at least one nanoporous shell disposed about the nanoporous core, the at least one nanoporous shell having a plurality of interconnected nanosized shell pores, and wherein the particles have a cubic crystal form with facets and a mean distribution of particle diameters in the assemblage with a standard deviation of less than 15%, and wherein the nanosized core pores and the nanosized shell pores have a diameter between 1 and 100 nm.

2. The assemblage of particles of claim 1 having at least two nanoporous shells disposed about the core.

3. The assemblage of particles of claim 1, wherein elementary composition of the particles comprises at least 90% of materials selected from the group consisting of metal oxides and metalloid oxides.

4. The assemblage of particles of claim 1, wherein the average particle size of the particles is greater than 1 micrometer.

5. The assemblage of particles of claim 1, wherein the interconnected nanosized shell pores of the at least one nanoporous shell comprise restrictions by covalent bonds between a molecule and the nanosized pore.

6. The assemblage of particles of claim 5, wherein the restrictions comprise at least one of organic molecules or polymers covalently bound to an inner surface of the interconnected nanosized shell pores of the at least one nanoporous shell.

7. The assemblage of particles of claim 5, wherein the restrictions comprise dextran or a derivative thereof.

8. The assemblage of particles of claim 1 further comprising an active substance in at least some of the interconnected nanosized core pores of the nanoporous core.

9. The assemblage of particles of claim 1, wherein elementary composition of the particles comprises at least 90% of silicon oxide.

10. The assemblage of particles of claim 8, wherein the active substance is selected from the group consisting of a biocide, a pharmaceutical, a perfume, a flavour, a fertilizer, and a plant hormone.

11. The assemblage of particles of claim 10, wherein the biocide is zinc pyrithione.

12. The assemblage of particles of claim 10, wherein the pharmaceutical is an antibiotic selected from the group consisting of gentamicin, vancomycin, and tobramycin.

13. The assemblage of particles of claim 10, wherein the pharmaceutical is a peptide hormone selected from the group consisting of leuprolide acetate, octreotide acetate, and triiodothyronine.

14. The assemblage of particles of claim 10, wherein the pharmaceutical is an antipsychotic selected from the group consisting of risperidone, flupentixol, and olanzapine.

15. The assemblage of particles of claim 10, wherein the pharmaceutical is an antineoplastic or anti-tumor drug selected from the group consisting of paclitaxel, etoposide, topotecan, cytarabine, cisplatin, and carboplatin.

16. The assemblage of particles of claim 10, wherein the pharmaceutical is a non-steroid anti-inflammatory selected from the group consisting of diclofenac and nabumethone.

17. The assemblage of particles of claim 10, wherein the pharmaceutical is an antidiabetic selected from the group consisting of risperidone, pioglitazone and gliclazide.

18. The assemblage of particles of claim 10, wherein the pharmaceutical is an analgetic selected from the group consisting of hydromorphone and buprenorphine.

19. The assemblage of particles of claim 10, wherein the pharmaceutical is testosterone.

20. The assemblage of particles of claim 10, wherein the pharmaceutical is rapamycin.

21. A method for the sustained release of an active substance to an environment comprising:
providing the assemblage of particles comprising an active substance of claim 9; and
placing said assemblage of particles in the environment; wherein the release of the active substance is sustained.

22. The method of claim 21, wherein the active substance is an active pharmaceutical ingredient.

23. A method for the manufacture of the assemblage of particles of claim 1 comprising:

mixing an ionic surfactant with an inorganic salt in hydrochloric acid;

mixing a co-solvent with a first non-ionic surfactant and a first silicon oxide source;

mixing the solution of the ionic surfactant and the inorganic salt with the solution of the first non-ionic surfactant and the first silicon oxide source in the first co-solvent in order to form the nanoporous core;

mixing a second co-solvent with a second non-ionic surfactant and a second silicon oxide source; and adding after a period of time the solution of the second co-solvent with the second non-ionic surfactant and the second silicon oxide source to the solution of the ionic surfactant and the inorganic salt and the first non-ionic surfactant and the first silicon oxide source in order to form the at least one nanoporous shell.

24. The method of claim 23, wherein the first or second silicon oxide source is a silane.

25. The method of claim 23, wherein the first or second co-solvent is selected from the group consisting of dimethyl acetamide, N,N-dimethylformamide, 1,3-dimethyl-3,4,5,6-tetrahydro-2(1H)-pyrimidinone, dimethyl sulfoxide, and N-methyl-2-pyrrolidone.

26. The method of claim 23, wherein the first or second non-ionic surfactant is a polyalkyleneoxide.

27. The method of claim 23, further comprising functionalising inner walls of at least some of the nanosized pores in the monodisperse particles.

28. The method of claim 23, further comprising adding an active substance to the monodisperse particles.

29. The method of claim 27, further comprising attaching restrictions to the functionalised inner walls by covalent bonding.

30. The method of claim 29, wherein the restrictions are formed of dextran polymers or derivatives thereof.

* * * * *